(12) United States Patent
Sakuma et al.

(10) Patent No.: US 9,297,730 B2
(45) Date of Patent: Mar. 29, 2016

(54) INDENTATION TEST METHOD AND INDENTATION TEST APPARATUS

(75) Inventors: Atsushi Sakuma, Tokyo (JP); Mitsuhiro Tani, Tokyo (JP)

(73) Assignee: NATIONAL UNIVERSITY CORPORATION TOKYO UNIVERSITY OF AGRICULTURE AND TECHNOLOGY, Fuchu-Shi (JP)

( * ) Notice: Subject to any disclaimer, the term of this patent is extended or adjusted under 35 U.S.C. 154(b) by 1023 days.

(21) Appl. No.: 13/138,235

(22) PCT Filed: Jan. 18, 2010

(86) PCT No.: PCT/JP2010/050499
§ 371 (c)(1),
(2), (4) Date: Oct. 10, 2011

(87) PCT Pub. No.: WO2010/084840
PCT Pub. Date: Jul. 29, 2010

(65) Prior Publication Data
US 2012/0022802 A1 Jan. 26, 2012

(30) Foreign Application Priority Data

Jan. 20, 2009 (JP) ................................ 2009-010426
Aug. 10, 2009 (JP) ................................ 2009-185525

(51) Int. Cl.
G01L 1/06 (2006.01)
G01L 1/04 (2006.01)
G06F 3/01 (2006.01)
G06F 3/03 (2006.01)
G01N 3/42 (2006.01)

(52) U.S. Cl.
CPC .......... *G01N 3/42* (2013.01); *G01N 2203/0075* (2013.01); *G01N 2203/0082* (2013.01); *G01N 2203/0089* (2013.01); *G01N 2203/0682* (2013.01)

(58) Field of Classification Search
CPC ....................................................... G01N 3/42
USPC ................. 702/42, 43, 81, 83, 179, 182, 183; 73/81; 435/7.1
See application file for complete search history.

(56) References Cited

U.S. PATENT DOCUMENTS

| 4,852,397 | A  | * | 8/1989  | Haggag ........................... 73/82 |
| 6,134,954 | A  | * | 10/2000 | Suresh et al. .................... 73/81 |
| 6,664,067 | B1 | * | 12/2003 | Hajduk et al. ................ 435/7.1 |
| 6,778,916 | B2 | * | 8/2004  | Lee ................................ 702/42 |
| 2003/0060987 | A1 | * | 3/2003 | Dao et al. ....................... 702/42 |

FOREIGN PATENT DOCUMENTS

| JP | 2003-044827 | 2/2003 |
| JP | 2004-361251 | 12/2004 |

* cited by examiner

*Primary Examiner* — Gregory J Toatley
*Assistant Examiner* — Felix Suarez
(74) *Attorney, Agent, or Firm* — Masuvalley and Partners

(57) ABSTRACT

A novel indentation test apparatus is provided. The indentation test apparatus is an apparatus for indenting a specimen with a spherical indenter. The indentation test apparatus includes a specimen thickness identifier) that identifies the thickness of the specimen, an equivalent indentation strain calculator that calculates equivalent indentation strain of the specimen by using the thickness of the specimen, and a Young's modulus calculator that calculates Young's modulus of the specimen by using the equivalent indentation strain. Young's modulus E of the specimen preferably ranges from 100 Pa to 100 MPa. The diameter of the spherical indenter preferably ranges from $1\times10^{-8}$ to 1 m.

14 Claims, 15 Drawing Sheets (a) Indentation depth (b) Second derivative of modulus (a) Modulus effect.  (b) Diameter effect.

(a) $\hat{F}$ curves.  (b) $\hat{E}$ curves.

Second derivative of modulus (a) Variation of Young's modulus.

(b) Variation of indenter diameter.

(a) Variation of Young's modulus.

(b) Variation of indenter diameter.

(a) Relationship of Young's modulus.

(b) Relationship of indenter diameter.

(a) Hardness A20.

(b) Hardness A30.

(c) Hardness A50.

INDENTATION TEST METHOD AND INDENTATION TEST APPARATUS

This application claims priority under 35 U.S.C. §371 as a National Stage application of international application number PCT/JP2010/050499, filed Jul. 18, 2010, entitled "INDENTATION TEST METHOD AND INDENTATION TEST APPARATUS," which claims priority to Japanese Patent Application No. JP2009-010426 Filed on Jan. 20, 2009, and Japanese Patent Application No. JP2009-185525, filed on Aug. 10, 2009 which are incorporated herein by reference.

TECHNICAL FIELD

The present invention relates to a novel indentation test method. The present invention further relates to a novel indentation test apparatus using the indentation test method.

BACKGROUND ART

A tensile test used to study deformation and other characteristics of a metallic material is a typical objective evaluation method but requires cutting a test piece off a bulk specimen, which makes the test highly invasive and makes it difficult to apply the test to the material of which a product is made and living biological tissue.

On the other hand, an indentation test also typically used in material hardness measurement allows noninvasive measurement because the test does not require cutting a test piece off a bulk specimen. It has been known in an indentation test that the Hertzian elastic contact theory can be used with metallic materials in a highly reliable manner (see Non-Patent Document 1, for example).

There have also been several indentation tests used to measure characteristics of a soft material that involves large deformation, such as biological soft tissue (see Non-Patent Documents 2 to 5, for example).

The present inventors have disclosed technical details associated with the invention (see Non-Patent Documents 6 to 9, for example).

TECHNICAL DOCUMENTS OF RELATED ART

Non-Patent Documents

Non-Patent Document 1: T. Sawa, Practical Material Mechanics, (2007), pp. 258-279, Nikkei Business Publications, Inc. (in Japanese)

Non-Patent Document 2: O. Takatani, T. Akatsuka, The Clinical Measurement Method of Hardness of Organism, Journal of the Society of Instrument and Control Engineers, Vol. 14, No. 3, (1975), pp. 281-291. (in Japanese)

Non-Patent Document 3: Y. Arima, T. Yano, Basic Study on Objectification of Palpation, Japanese Journal of Medical Electronics and Biological Engineering, Vol. 36, No. 4, (1998), pp. 321-336. (in Japanese)

Non-Patent Document 4: N. E. Waters, The Indentation of Thin Rubber Sheets by Spherical indentors, British Journal of Applied Physics, Vol. 16, Issue 4, (1965), pp. 557-563.

Non-Patent Document 5: T. Ishibashi, S. Shimoda, T Furukawa, I. Nitta and H. Yoshida, The Measuring Method about Young's Modulus of Plastics Using the Indenting Hardness Test by a Spherical Indenter, Transactions of the Japan Society of Mechanical Engineers, Series A, Vol. 53, No. 495, (1987), pp. 2193-2202. (in Japanese)

Non-Patent Document 6: M. Tani, A. Sakuma, M. Ogasawara, M. Shinomiya, Minimally Invasive Evaluation of Mechanical Behavior of Biological Soft Tissue using Indentation Testing, No. 08-53, (2009), pp. 183-184.

Non-Patent Document 7: M. Tani, A. Sakuma, Measurement of Thickness and Young's Modulus of Soft Materials by using Spherical Indentation Testing, No. 58, (2009), pp. 365-366.

Non-Patent Document 8: A. Sakuma, M. Tani, Spherical Indentation Technique for Low-invasive Measurement for Young's Modulus of Human Soft Tissue, No. 09-3, (2009), pp. 784-785.

Non-Patent Document 9: M. Tani and A. Sakuma, M. Shinomiya, Evaluation of Thickness and Young's Modulus of Soft Materials by using Spherical Indentation Testing, Transactions of the Japan Society of Mechanical Engineers, Series A, Vol. 75, No. 755, (2009), pp. 901-908. (in Japanese)

SUMMARY OF THE INVENTION

Problem to be Solved by the Invention

In the measurement of characteristics of a soft material that involves large deformation, such as biological soft tissue, made in an indentation test described above, although Toshiyuki Sawa showed that the Hertzian elastic contact theory provides a high reliability, the high reliability only valid within a minute deformation range. Osamu Takatani et al. applied an indentation test to biological soft tissue but the test is based on an N-value approach essentially equivalent to the Hertzian elastic contact theory. Further, Yoshitaka Arima et al. reported an approach in which identification is made based on energy loss in loading and unloading processes along with an N-value approach, but a semi-infinite body is assumed as in the Hertzian elastic contact theory and no influence of thickness is considered. N. E. Waters reported a study on the influence of thickness, but the report described only the influence of thickness but does not describe any evaluation taking into account a stress-strain relationship. Tatsuya Ishibashi et al. reported that an indentation test was applied to a polymer material in consideration of an irreversible behavior, but the method is hardly applied to a soft material having high reversibility.

There is therefore a desire to solve the problems described above and develop a novel indentation test method and indentation test apparatus.

The invention has been made in view of the problems described above, and an object of the invention is to provide a novel indentation test method.

Another object of the invention is to provide a novel indentation test apparatus using the indentation test method.

Means for Solving the Problem

To solve the problems described above and achieve the objects of the invention, an indentation test method according to the invention is a method for indenting a specimen with an indenter, the method comprising calculating an equivalent indentation strain of the specimen by using the thickness of the specimen and calculating Young's modulus of the specimen by using the equivalent indentation strain.

The indentation test method preferably, but not necessarily, further comprises identifying the thickness of the specimen. The indenter is preferably, but not necessarily, a spherical indenter. The diameter of the spherical indenter preferably, but not necessarily, ranges from $1\times10^{-8}$ to 1 m. The identification of the thickness of the specimen is preferably, but not necessarily, performed by calculation based on the diameter of the spherical indenter, Young's modulus at the time of contact, and the second derivative of Young's modulus.

An indentation test apparatus according to the invention is an apparatus for indenting a specimen with an indenter, the apparatus comprising an equivalent indentation strain calculator that calculates an equivalent indentation strain of the specimen by using the thickness of the specimen and a Young's modulus calculator that calculates the Young's modulus of the specimen by using the equivalent indentation strain.

The indentation test apparatus preferably, but not necessarily, further comprises a specimen thickness identifier that identifies the thickness of the specimen. The indenter is preferably, but not necessarily, a spherical indenter. The diameter of the spherical indenter preferably, but not necessarily, ranges from $1 \times 10^{-8}$ to 1 m. The identification of the thickness of the specimen is preferably, but not necessarily, performed by calculation based on the diameter of the spherical indenter, Young's modulus at the time of contact, and the second derivative of Young's modulus at the time of contact.

Advantages of the Invention

The invention provides the following advantages:

The indentation test method according to the invention can be a novel indentation test method because equivalent indentation strain of a specimen is calculated by using the thickness of the specimen and Young's modulus of the specimen is calculated by using the equivalent indentation strain.

The indentation test apparatus according to the invention can be a novel indentation test apparatus because the apparatus includes an equivalent indentation strain calculator that calculates equivalent indentation strain of a specimen by using the thickness of the specimen and a Young's modulus calculator that calculates Young's modulus of the specimen by using the equivalent indentation strain.

MODES FOR CARRYING OUT THE INVENTION

An indentation test method and an indentation test apparatus according to a first embodiment the invention will be described below.

The indentation test method, which is a method for indenting a specimen with a spherical indenter, includes identifying the thickness of the specimen, calculating an equivalent indentation strain of the specimen by using the thickness of the specimen, and calculating a Young's modulus of the specimen by using the equivalent indentation strain.

The indentation test apparatus, which is an apparatus for indenting a specimen with a spherical indenter, includes a specimen thickness identifier that identifies the thickness of the specimen, an equivalent indentation strain calculator that calculates an equivalent indentation strain of the specimen by using the thickness of the specimen, and a Young's modulus calculator that calculates a Young's modulus of the specimen by using the equivalent indentation strain.

In the texts in the present specification, an alphabet with a hat character is described as "(alphabet) hat", an alphabet with an overline is described as "(alphabet) overline", and an alphabet with a second differential coefficient is described as "(alphabet) second differential coefficient".

A description will be made of how to evaluate an indentation test. Contact deformation of a finite specimen will first be described.

Figure 1:
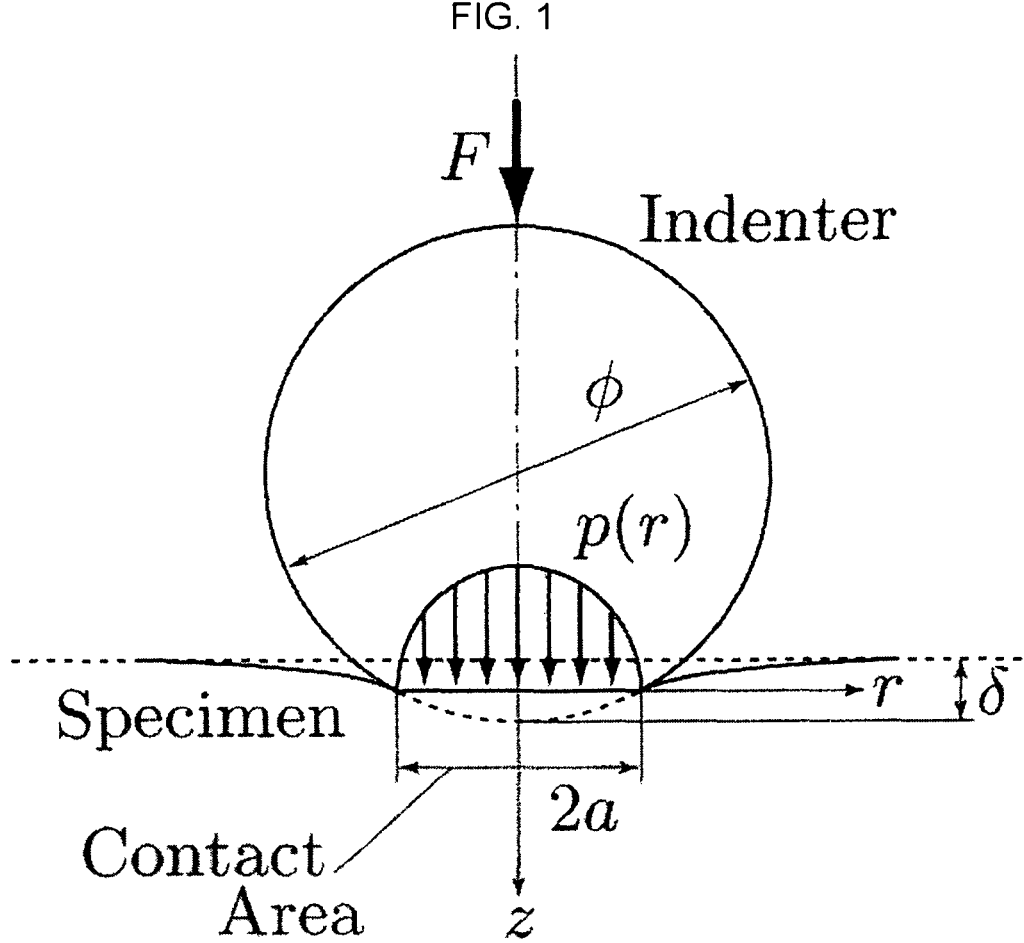
FIG. 1 shows a state in which a spherical indenter comes into contact with a specimen having a flat surface.

When a sufficiently hard spherical indenter indents a semi-infinite specimen, the relationship between an indentation force F and an indentation depth δ shown in FIG. 1 is derived from the Hertzian elastic contact theory as follows:

[Equation 1]

$$F = \frac{4}{3}\frac{E}{1-v^2}\left(\frac{\phi}{2}\right)^{\frac{1}{2}}\delta^{\frac{3}{2}} = A\delta^{\frac{3}{2}} \qquad (1)$$

In Equation (1), the coefficient A is expressed as follows:

[Equation 2]

$$A = \frac{4}{3}\frac{E}{1-v^2}\left(\frac{\phi}{2}\right)^{\frac{1}{2}} \qquad (2)$$

In Equation (2), φ, E, and ν are the diameter of the spherical indenter, Young's modulus of the specimen, and the Poisson ratio, respectively. Further, the force distributed across a contact area having a radius "a" shown in FIG. 1 is assumed to have a force distribution p(r), a function of the radius "r", across the surface of the specimen on which the force acts. The stress σ at the center of the contact area is expressed as follows:

[Equation 3]

$$\sigma = \frac{3}{2\pi}F^{\frac{1}{3}}\left\{\frac{3}{4}\frac{1-v^2}{E}\left(\frac{\phi}{2}\right)\right\}^{-\frac{2}{3}} \qquad (3)$$

Young's modulus E is derived as a function of the indentation force F and strain ε from Equation (3) and Hooke's law σ=Eε as follows:

[Equation 4]

$$E = \frac{6}{\pi^3(1-v^2)^2}\left(\frac{2}{\phi}\right)^2\frac{F}{\varepsilon^3} \qquad (4)$$

From Equations (1) and (4), the strain induced by the contact between the semi-infinite specimen and the rigid sphere is uniquely determined based on the diameter φ of the indenter and the indentation depth δ as follows:

[Equation 5]

$$\overline{\varepsilon}_H = \frac{2}{\pi(1-v^2)}\left(\frac{2\delta}{\phi}\right)^{\frac{1}{2}} \qquad (5)$$

The $\overline{\varepsilon}_H$ (overline) is called the Hertz strain.

Figure 2:
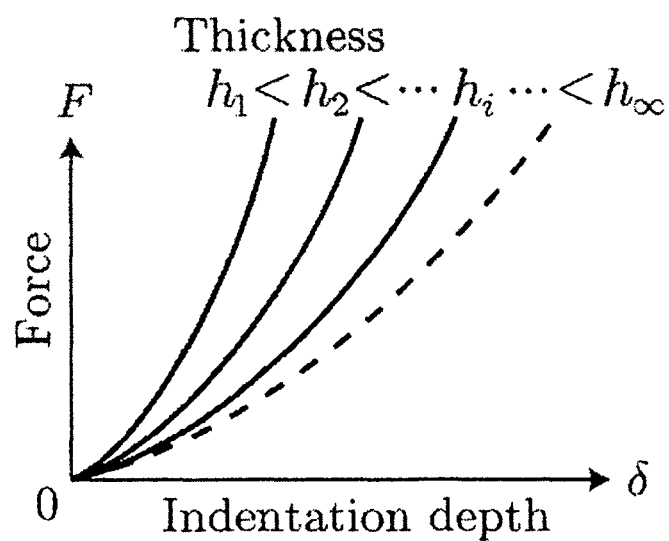
FIG. 2 shows the relationship between a force and an indentation depth.

Now, consider an indentation test in which a spherical indenter indents a specimen placed on a rigid body and having a variety of thicknesses hi (i=1, 2, . . . , ∞). Force F-indentation depth δ curves shown in FIG. 2 are obtained in consideration of an influence of the rigid body, which is on the opposite side to the surface on which the force acts from the indenter. In an indentation test conducted on a semi-infinite specimen having an infinite thickness $h_\infty$, the force F curve, which is explained by the Hertzian elastic contact theory, is indicated by the broken line, whereas in an indentation test conducted on a finite specimen, the force F (hat) is typically greater than that for the semi-infinite specimen as follows:

[Equation 6]

$$\hat{F} > F \qquad (6)$$

Assume now that the Hertzian elastic contact theory can be applied to the force F (hat), which is influenced by the difference in the thickness hi of the specimen. From Equation (1), the force F (hat) is expressed as follows:

[Equation 7]

$$\hat{F} = \hat{A}\delta^{3/2} \qquad (7)$$

The coefficients A and A (hat) associated with the indentation depth δ therefore have the following relationship:

[Equation 8]

$$\hat{A} > A \qquad (8)$$

Further, assume that the diameter φ of the indenter and the Poisson ratio ν of the specimen do not change. Equation (2) then provides the following relationship. That is, Young's modulus E (hat) determined by applying the Hertzian elastic contact theory to the result of the indentation test conducted on any of the finite specimens is greater than the intrinsic Young's modulus E.

[Equation 9]

$$\hat{E} > E \qquad (9)$$

Thus, the determined Young's modulus E (hat) is called a spherical indentation modulus.

When Equation (1) derived from the Hertzian elastic contact theory based on a semi-infinite specimen is applied to a finite specimen, the spherical indentation modulus E (hat) is influenced by the thickness hi, as shown in Equation (9). Consider now using the influence to identify the thickness hi of the specimen.

In the identification of the spherical indentation modulus E (hat), it is believed that the difference in the thickness hi of the specimen influences little the spherical indentation modulus E (hat) at the instant of contact when the amount of deformation is very small. That is, at the instant of contact, the following relationship for an arbitrary thickness hi can be derived from the condition under which Equation (1) is applied:

[Equation 10]

$$\lim_{\delta \to 0}\frac{\partial \hat{E}(h_i)}{\partial \delta} = 0 \qquad (10)$$

Figure 3:
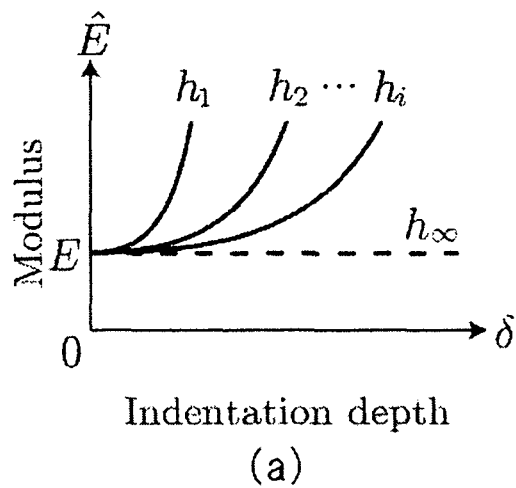
FIG. 3(a) shows the relationship between a spherical indentation modulus and the indentation depth.
FIG. 3(b) shows the relationship between the thickness of the specimen and the second derivative of the spherical indentation modulus.
Figure 3:
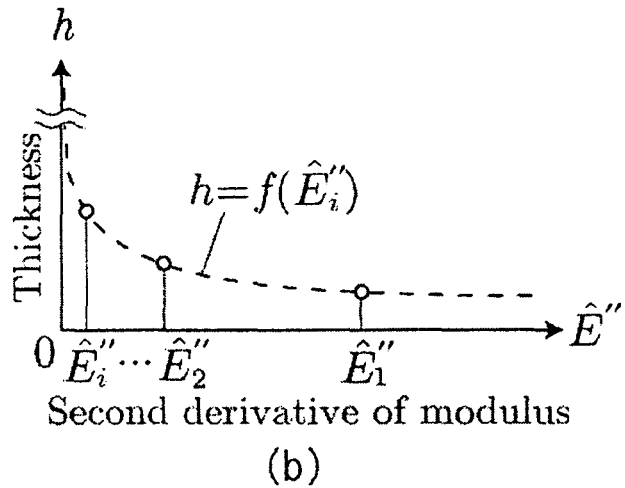

On the other hand, when the thickness hi of the specimen is smaller, the influence of the rigid body under the specimen appears earlier. As a result, when the thickness hi of the specimen is smaller, the identified spherical indentation modulus E (hat) increases more steeply as the indentation proceeds, as indicated by the solid lines in FIG. 3(*a*). When the thickness of the specimen satisfies hi<hi+1, the increase is expressed by the following relationship:

[Equation 11]

$$\lim_{\delta \to 0} \frac{\partial^2 \hat{E}(h_i)}{\partial \delta^2} > \lim_{\delta \to 0} \frac{\partial^2 \hat{E}(h_{i+1})}{\partial \delta^2} \tag{11}$$

The following relationship is therefore conceivable between the thickness hi of the specimen and the second derivative of the spherical indentation modulus E (hat) (second differential coefficient):

[Equation 12]

$$h = f(\hat{E}'') \tag{12}$$

If the function f(E(hat) (second differential coefficient)) shown in FIG. 3(b) can be obtained, the thickness hi of the specimen can be derived from information obtained when the contact starts.

How to evaluate indentation deformation will be described. The process of indenting a soft material involves a phenomenon in which a deformed region in the specimen greatly changes as the indenter indents the specimen, like the shape of the surface on which the force acts greatly changes. In view of the phenomenon, the indentation deformation is considered as the superposition of the contact deformation due to the spherical indenter and the compression deformation.

In this process, first express the effect of the contact by using the Hertz strain $\bar{\epsilon}_H$ (overline), and assume that the compression is expressed by the rate $\bar{\epsilon}_V$ (overline) of change in the volume of the region influenced by compression deformation that occurs because the specimen is soft. The following relationship is then defined:

[Equation 13]

$$\bar{\epsilon}_I = \bar{\epsilon}_H + \bar{\epsilon}_V \tag{13}$$

In Equation (13), $\epsilon_I$ (overline), which is a three-dimensional strain distribution induced in the specimen during the indentation process, is expressed by using an equivalent uniaxial strain and called the equivalent indentation strain.

Figure 4:
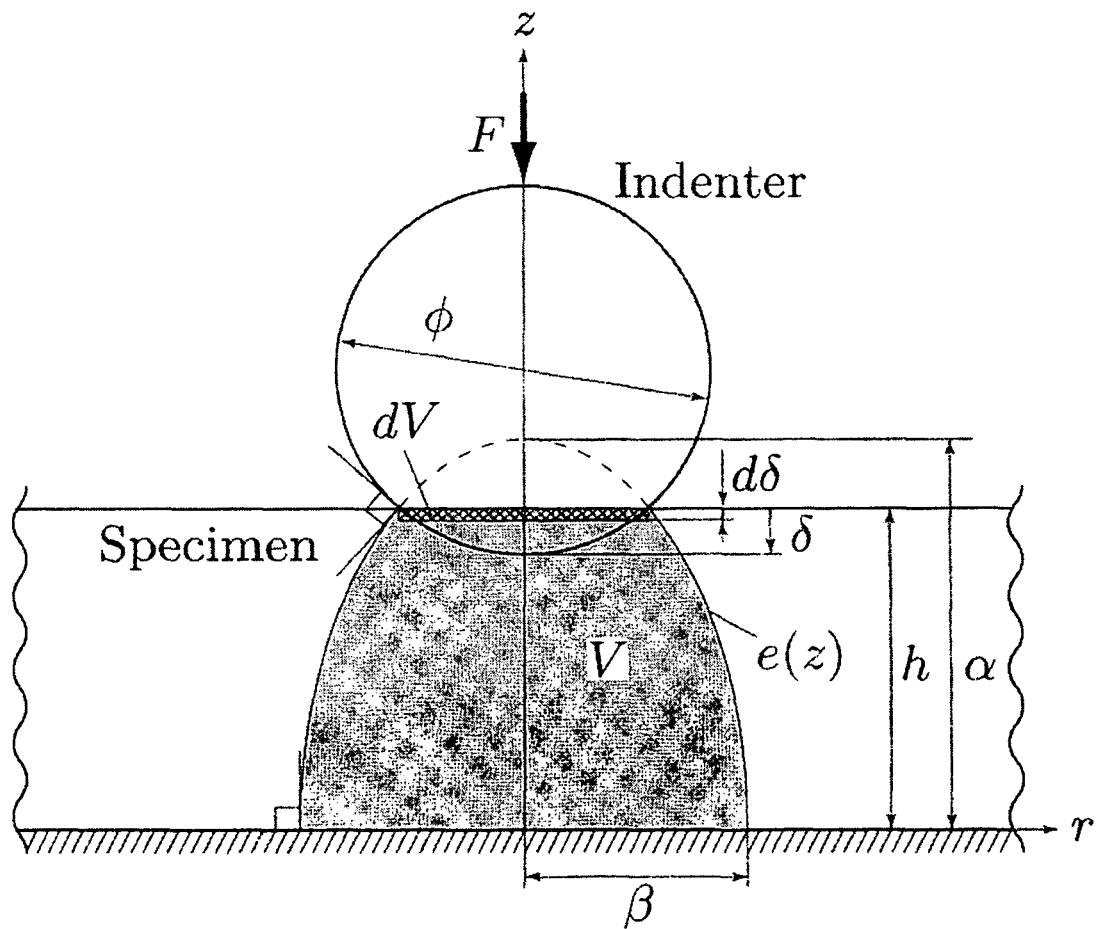
FIG. 4 shows a compressed region having a spheroid shape.

In the indentation process of indenting a soft material with a spherical indenter, consider a compressed region V in the specimen that is deformed due to a particularly large force. In the region V, consider a spheroid not only perpendicular to the indenter sphere surface containing the line of intersection of the initial surface of the specimen and the surface of the indenter but also perpendicular to a lower interface of the specimen. The spheroid is hatched in FIG. 4. The spheroid is expressed as a function of not only the distance 13 from a force axis z to the line where the spheroid intersects the lower interface but also the height a of the spheroid as follows:

[Equation 14]

$$e(z) = \frac{\beta}{\alpha}\sqrt{\alpha^2 - z^2} \tag{14}$$

The volume V of the compressed region can be expressed by the following equation:

[Equation 15]

$$V = \int_0^h \pi e(z)^2 dz = \frac{\pi}{3}(\phi\delta - \delta^2)\frac{2h^2 + 3h\left(\frac{\phi}{2} - \delta\right)}{\frac{\phi}{2} - \delta} \tag{15}$$

The strain induced in the compressed region can be determined from the change in the compressed region dV. Consider a simple method for expressing the change in the compressed region dV by using the amount of shift dδ of the upper surface of the compressed region. The change in the compressed region dV can be expressed by using the amount of shift dδ as follows:

[Equation 16]

$$dV = \pi e(h)^2 d\delta = \pi(\phi\delta - \delta^2)d\delta \tag{16}$$

Further, an increment $d\bar{\epsilon}_V$ (overline) of the rate $\bar{\epsilon}_V$ (overline) of change in the compressed region V can be defined by the following equation:

[Equation 17]

$$d\bar{\epsilon}_V = \frac{dV}{V} \tag{17}$$

The strain $\bar{\epsilon}_V$ (overline) induced in the compressed region can therefore be expressed by the following equation:

[Equation 18]

$$\bar{\epsilon}_V = \int_0^\delta d\bar{\epsilon}_V = \frac{\delta}{h} + \frac{2}{3}\ln\left\{\frac{2h + 3\left(\frac{\phi}{2} - \delta\right)}{2h + 3\frac{\phi}{2}}\right\} \tag{18}$$

Based on Equation (18), the equivalent indentation strain $\bar{\epsilon}_I$ (overline) expressed by Equation (13) is expressed as follows:

[Equation 19]

$$\bar{\epsilon}_I = \frac{2}{\pi(1-\nu^2)}\left(\frac{2\delta}{\phi}\right)^{\frac{1}{2}} + \frac{\delta}{h} + \frac{2}{3}\ln\left\{\frac{2h + 3\left(\frac{\phi}{2} - \delta\right)}{2h + \frac{3}{2}\phi}\right\} \tag{19}$$

Assuming that the diameter φ of the indenter is infinite, the equivalent indentation strain $\bar{\epsilon}_I$ (overline) is expressed as follows:

[Equation 20]

$$\lim_{\phi \to \infty} \bar{\epsilon}_I = \frac{\delta}{h} \tag{20}$$

The equivalent indentation strain $\bar{\epsilon}_I$ (overline) is thus uniaxial nominal strain. On the other hand, if the thickness h is infinite, the equivalent indentation strain $\bar{\epsilon}_I$ (overline) is expressed as follows:

[Equation 21]

$$\lim_{h \to \infty} \bar{\varepsilon}_I = \frac{2}{\pi(1-v^2)}\left(\frac{2\delta}{\phi}\right)^{\frac{1}{2}} = \bar{\varepsilon}_H \quad (21)$$

The equivalent indentation strain $\varepsilon_I$ (overline) now agrees with the Hertz strain $\varepsilon_H$ (overline).

The equivalent indentation strain $\varepsilon_I$ (overline) expressed by Equation (19) is therefore found to be capable of representing both the contact deformation and the compression deformation.

Assuming that the equivalent indentation strain $\varepsilon_I$ (overline) expressed by Equation (19) can equivalently express uniaxial deformation, the stress σ induced in the specimen can be expressed as follows:

[Equation 22]

$$\sigma = E\bar{\varepsilon}_I \quad (22)$$

Further, assuming that Equation (3) is satisfied between the stress σ and the force F (hat) at the contact area, Young's modulus E of the specimen can be derived by using the equivalent indentation strain $\varepsilon_I$ (overline) as follows:

[Equation 23]

$$E = \frac{6}{\pi^3(1-v^2)^2}\left(\frac{2}{\phi}\right)^2 \frac{\hat{F}}{\bar{\varepsilon}_I^3} \quad (23)$$

Using Equation (23) and Equation (19), which expresses the equivalent indentation strain $\varepsilon_I$ (overline), along with the method for determining the thickness hi of the specimen described above allows Young's modulus E of the specimen to be evaluated in theory based on the diameter φ of the spherical indenter, the force F (hat), and the indentation depth δ.

Indentation tests will next be conducted on specimens having known Young's modulus and a plurality of thicknesses to check the validity of the assumptions made above.

Experimental validation of the evaluation method will be described. An indentation test apparatus and conditions under which the apparatus operates will first be described.

Figure 5:
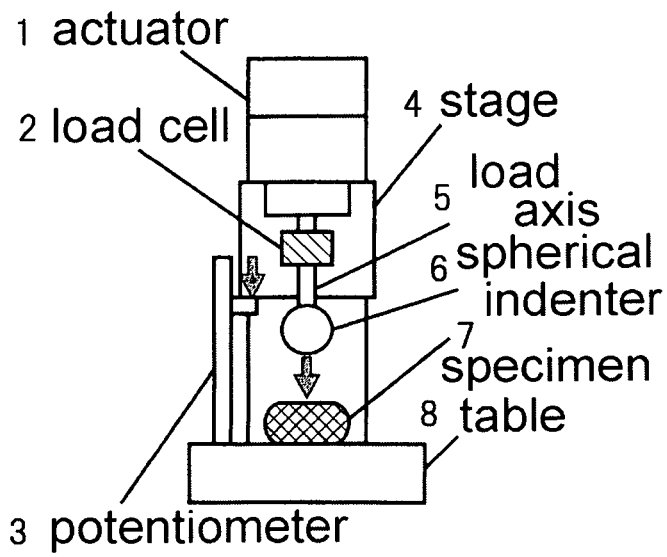
FIG. 5 schematically shows an indentation test apparatus.

To check that the same Young's modulus can be identified by indentation tests conducted on the specimens having different thicknesses, an indentation test apparatus shown in FIG. 5 is used. The indentation test apparatus is so configured that a PC controls a load axis 5 attached to an actuator 1 (manufactured by NSK, Model: XY-HRS400-RH202) that operates at a rate of 1.2 m/s at maximum. A load cell 2 (manufactured by Kyowa Electronic Instruments Co., Ltd., Model: LURA100NSA1) attached to the axis produces a load, and a potentiometer 3 (manufactured by Alps Electric Co., Ltd., Model: Slide Volume RSA0N11S9002) measures the indentation depth in the form of travel of a stage 4 of the actuator 1, to which an indenter is attached.

Figure 6:
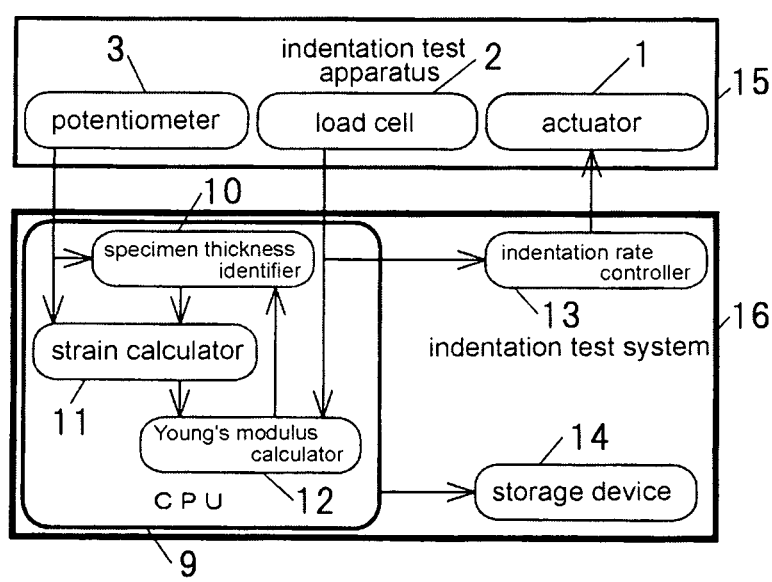
FIG. 6 shows the configuration of an indentation test system.

An indentation test system 16 calculates a Young's modulus based on the magnitude of the force F sent from the load cell 2 and the indentation depth δ sent from the potentiometer 3 in the indentation test apparatus 15, as shown in FIG. 6. An indentation rate controller 13 in the indentation test system 16 controls the operation of the indentation test apparatus 15 at the same time. The thickness of a specimen is identified based on the thus sent indentation depth δ and the calculated Young's modulus. Based on the identified and calculated thickness of the specimen, strain is calculated in consideration of the influence of the thickness of the specimen, and the Young's modulus is calculated in consideration of the influence of the thickness of the specimen. The data handled by a CPU 9 are all recorded in a storage device 14.

As for a specimen, a polyurethane resin, which has excellent moldability and stable physical properties and is hence used as a pseudo biological specimen, is selected as a soft material. Among a variety of polyurethane resins, a sheet of commercially available vibration-resistant mat material having low elasticity and high viscosity and manufactured by Peacelogi is used. The shape of the sheet material is $80 \times 10^{-3}$ m in vertical length, $80 \times 10^{-3}$ m in horizontal length, and about $4 \times 10^{-3}$ m in thickness. A rectangular column-shaped specimen is cut off a single sheet of the material and used in a tensile test conducted for validation purposes, and specimens having different thicknesses are prepared for indentation tests by bonding an arbitrary number of specimens with the aid of the viscosity of the specimens themselves. Table 1 shows measured thicknesses of the thus prepared specimens. As for the spherical indenter used in the indentation tests, an acrylic sphere having a diameter φ of $2.0 \times 10^{-2}$ m, which can be used in the human body in a future experiment, is used. The adhesion between the acrylic sphere and the specimen that come into contact with each other is reduced by applying talc powder onto the contact surface of the specimen. The slowest indentation rate available in the apparatus specifications is selected to minimize the influence of the viscosity of the polyurethane resin.

TABLE 1

| Conditions of indentation test | | | |
|---|---|---|---|
| Thickness h, $10^{-3}$ m | 3.8 | 10.7 | 17.8 |
| | 24.7 | 31.3 | 39.2 |
| Dia. of indenter φ, m | | 0.02 | |
| Indentation rate, m/s | | $1.0 \times 10^{-4}$ | |

Young's modulus obtained in the tensile test will next be described. Results obtained in the tensile test are presented to validate the results obtained in the indentation tests. Table 2 shows conditions under which the tensile test is conducted. In particular, since the tensile rate was set at $1.0 \times 10^{-4}$ m/s, which is the slowest rate available in the apparatus specifications, the rate of strain was 0.005/sec.

TABLE 2

| Conditions of tensile test | |
|---|---|
| Gauge length, m | 0.02 |
| Tensile rate, m/s | $1.0 \times 10^{-4}$ |

Figure 7:
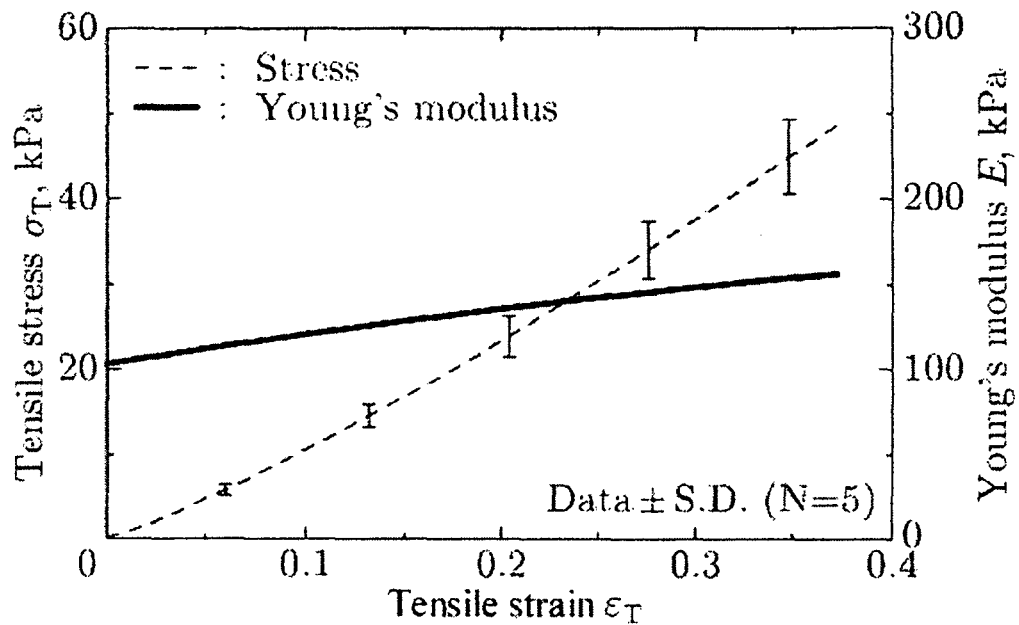
FIG. 7 shows results of a tensile test.

FIG. 7 shows results of the tensile test conducted under the conditions described above. The number of specimens N used in the tensile test is five, and the stress shown in FIG. 7 is a true stress calculated by using a Poisson ratio ν of 0.4, which is a typical value for a polyurethane resin, and by assuming that the cross-sectional area of each specimen changes in the loading process. The resultant curve indicated by the broken line is slightly convex downward. Young's modulus E determined from the curve is indicated by the solid line, which shows not only an increase in strain $\varepsilon_T$ resulting from tensile stress but also a hardening of the specimens.

An influence of the thickness of a specimen on the magnitude of the indentation force will next be described. In this description, an influence of the thickness of a specimen on the magnitude of the force obtained in an indentation test is evaluated.

Figure 8:
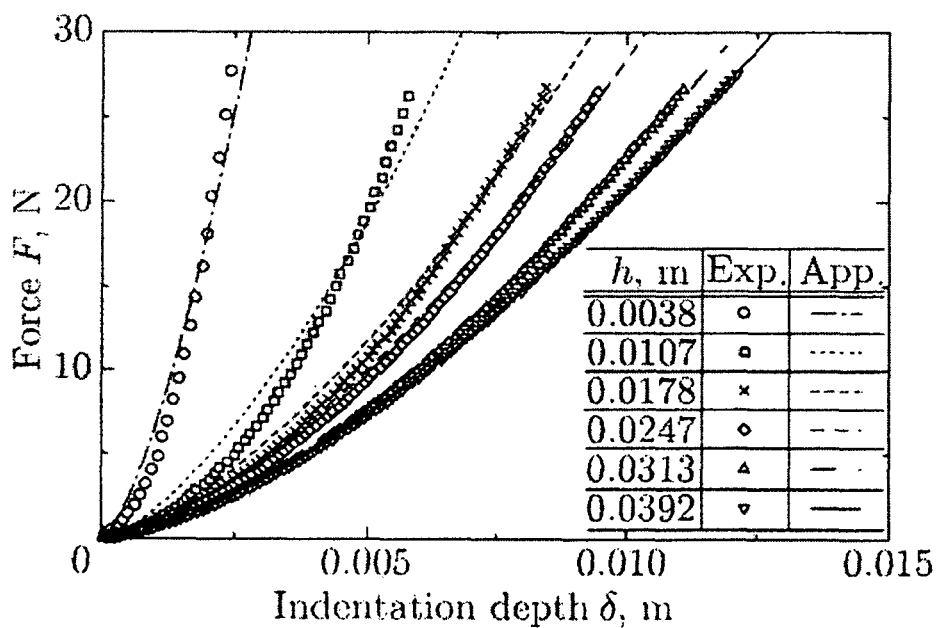
FIG. 8 shows the relationship between the indentation depth δ and the force F obtained in indentation tests and also shows curves representing the test results having undergone least squares approximation based on an equation derived from the Hertzian elastic contact theory.

FIG. 8 shows the relationship between the indentation depth δ and the force F obtained in the indentation tests conducted on the specimens having the thicknesses shown in Table 1. FIG. 8 also shows curves representing the test results having undergone least squares approximation based on Equation (1) derived from the Hertzian elastic contact theory.

As seen from the results, a smaller thickness hi of the specimen causes the indentation force to significantly increase as shown in FIG. 2, and curves obtained from Equation (1) based on the Hertzian elastic contact theory, which are relatively close to experimental results when the thickness hi of the specimen is large, more greatly differ from experimental results when the thickness hi of the specimen is smaller.

Based on the results, to express the significant increase in the indentation force, an equation containing a coefficient B expressing the influence of the increase in the indentation force is derived as follows:

[Equation 24]

$$\hat{F} = A\{\delta(1+B\delta)\}^{3/2} = \hat{A}\delta^{3/2} \quad (24)$$

Figure 9:
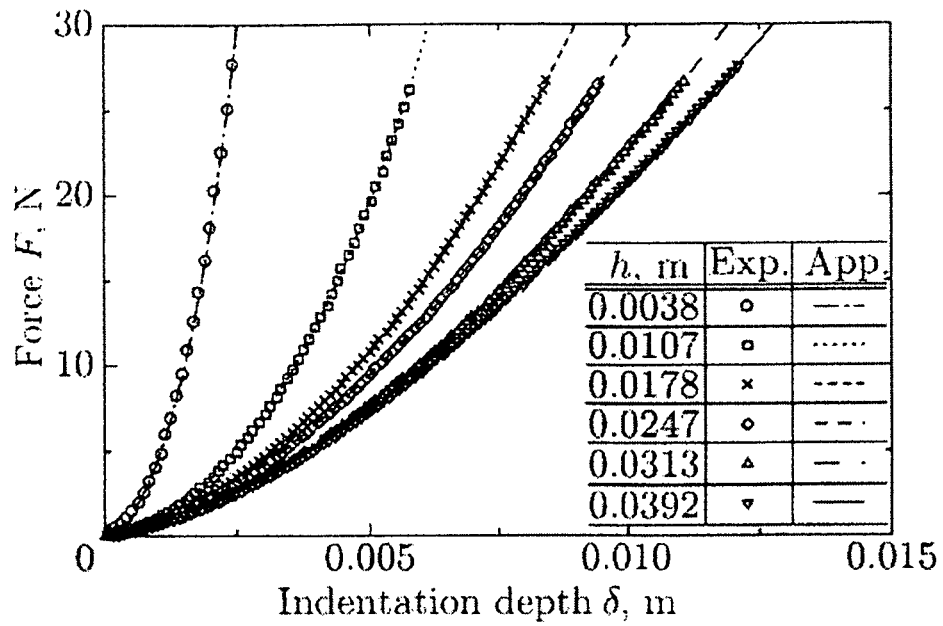
FIG. 9 shows the relationship between the indentation depth δ and the force F obtained in the indentation tests and also shows curves representing the test results having undergone least squares approximation based on an equation containing a coefficient expressing the influence of increase in the force.

FIG. 9 shows the same results as those in FIG. 8 with curves representing the results having undergone a least squares approximation based on Equation (24) instead of those obtained from Equation (1). Table 3 shows the values of the coefficient B.

TABLE 3

| Values of coefficient B | | | | | | |
|---|---|---|---|---|---|---|
| | Thickness h, $10^{-3}$ m | | | | | |
| | 3.8 | 10.7 | 17.8 | 24.7 | 31.3 | 39.2 |
| Parameter B, /m | 407.0 | 135.2 | 26.3 | 5.6 | 1.8 | 0.2 |

As seen from the results shown in FIG. 9, Equation (24) provides approximation results that differ less from experimental results than in FIG. 8. When Equation (24) is used, the following relationship is satisfied between the Young's modulus E and the spherical indentation modulus E (hat):

[Equation 25]

$$E(1+B\delta)^{3/2} = \hat{E} \quad (25)$$

Equation (25) corresponds to the relationship shown in FIG. 3(a).

A description will now be made of a study on how to derive the thickness of a specimen. Based on the results of the indentation test described above that are influenced by the thickness hi of the specimens, a method for determining the thickness hi of the specimens will be discussed.

Figure 10:
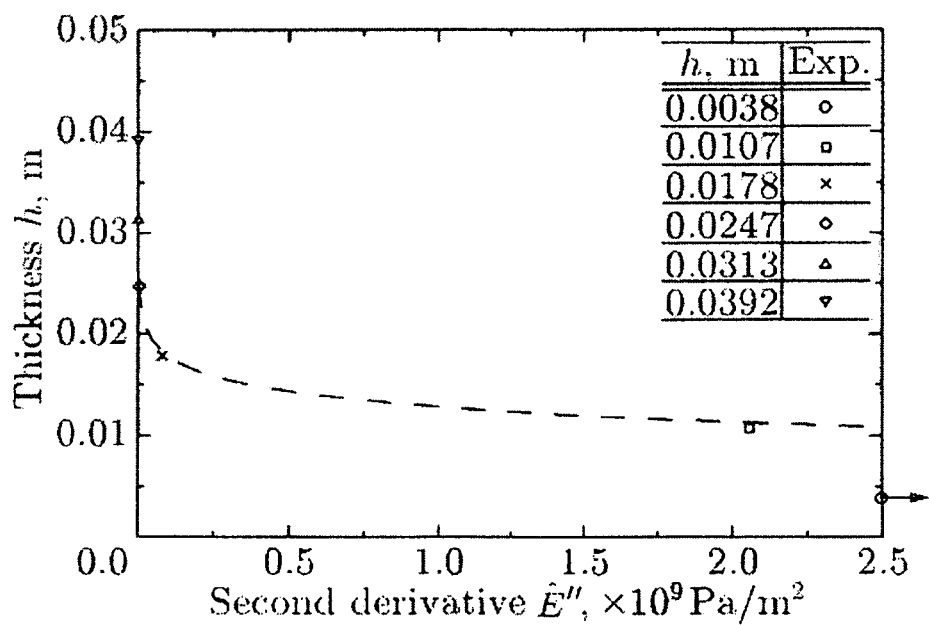
FIG. 10 shows the relationship between the second derivative of a spherical indentation modulus and the thickness of a specimen.
Figure 11:
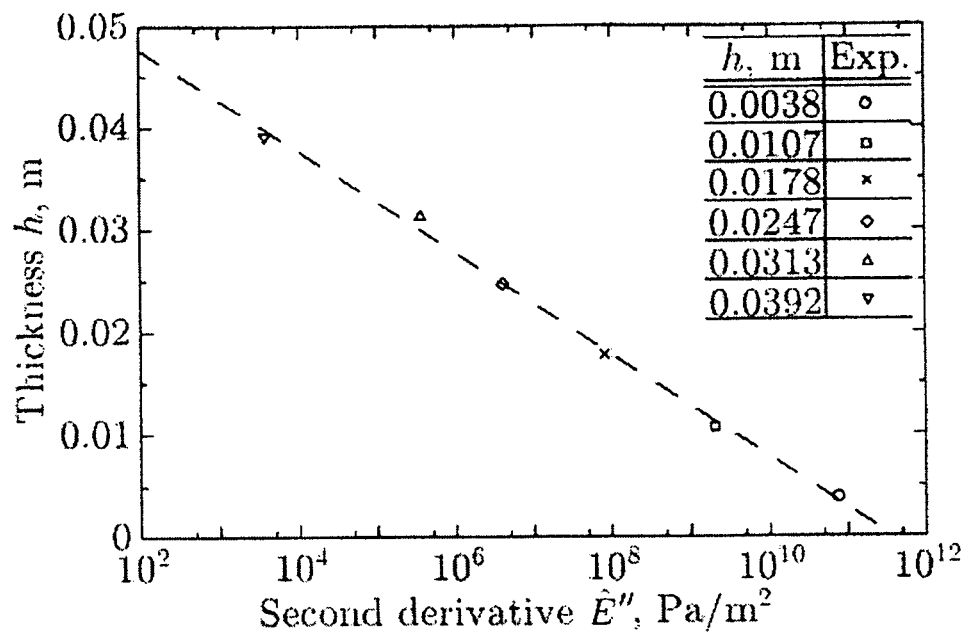
FIG. 11 shows the relationship between the second derivative of the spherical indentation modulus and the thickness of a specimen but with the axis representing the second derivative in a logarithmic scale.

FIGS. 10 and 11 first show the second derivative of the spherical indentation modulus E (hat) (second differential coefficient) determined by using Equations (24) and (25). The relationship between the indentation force F (hat) and the indentation depth δ obtained in the tests is approximated by using a function one example of which is Equation (24). Using the function (24) and Equations (1) and (2) allows Equation (25) to define the spherical indentation modulus E (hat). Young's modulus E is determined by Equation (25). FIG. 10 shows the relationship between the second derivative E (hat) (second differential coefficient) and the thickness hi of the specimen, and the second derivative E (hat) (second differential coefficient) increases exponentially as the thickness hi of the specimen decreases. The broken line in FIG. 10 is obtained by approximating the results by using the following exponential function:

[Equation 26]

$$h(\hat{E}'') = H\ln\left(\frac{G}{\hat{E}''}\right) \quad (26)$$

FIG. 11 shows the same results as those shown in FIG. 10 but with the axis representing the second derivative E (hat) (second differential coefficient) in a logarithmic scale. Table 4 shows the values of the coefficients H and G.

[Table 4]

TABLE 4

| Values of coefficients H and G | |
|---|---|
| H, m | $2.16 \times 10^{-3}$ |
| G, Pa/m$^2$ | $3.76 \times 10^9$ |

The results shows that there is a strong exponential relationship between the thickness hi of the specimens and the second derivative E (hat) (second differential coefficient) in the indentation tests using the spherical indenter, and the thickness hi can be determined based on the relationship. The thickness hi of the specimens will be identified by using Equation (26).

A description will be made of a method for identifying Young's modulus even if the thickness of a specimen varies. In the method, the thickness of a specimen is determined by using the method described above and/or any other method, and the Young's modulus is identified in consideration of the information on the thickness of the specimen even if the thickness of the specimen varies.

Figure 12:
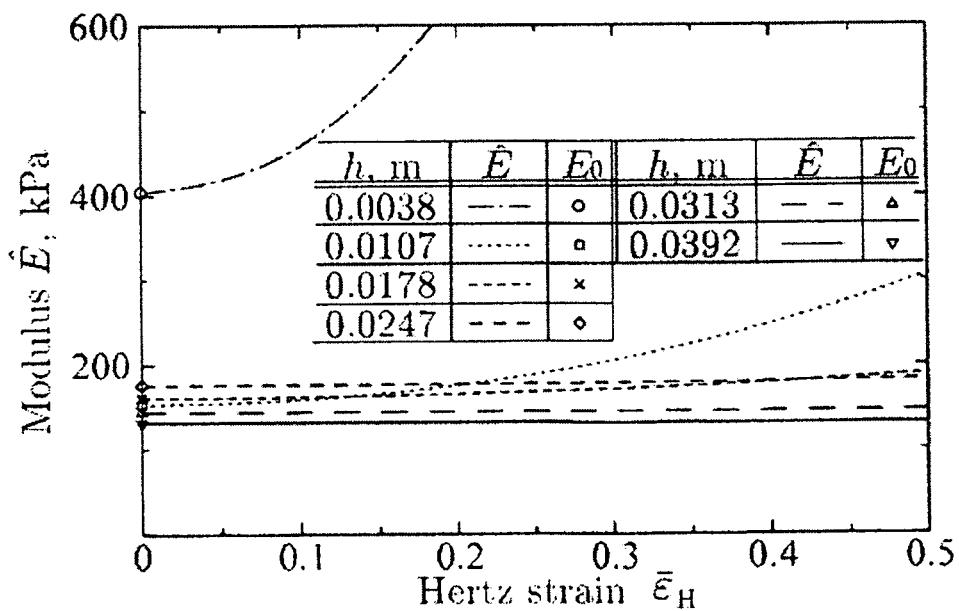
FIG. 12 shows the relationship between the spherical indentation modulus and Hertz strain.

First, FIG. 12 shows the spherical indentation modulus E (hat) determined by using Equation (4), which is based on the Hertzian elastic contact theory, versus Hertz strain $\epsilon_H$ (overline) expressed by Equation (5), which is a function monotonously increasing with respect to the indentation depth δ. The spherical indentation modulus E (hat) is determined from Equation (4) based on the measured force F and the Hertzian strain $\epsilon_H$ (overline) determined from Equation (5) based on the indentation depth δ.

The study was conducted by assuming the Poisson ratio ν that has not been measured to be 0.4 for convenience and setting the indentation depth δ to be smaller than or equal to 0.01 m so that it does not exceed the radius of the indenter. From the result of the study, the Young's modulus $E_0$, which is the modulus for zero strain at the time of contact and determined by Equation (25), is significantly high for the specimen having the smallest thickness hi. It is therefore difficult to identify the spherical indentation modulus E (hat) in an indentation process when the thickness hi of the specimen is very small. Further, the derived spherical indentation modulus E (hat) indicated by the lines in FIG. 12 increases as the indentation proceeds, as in FIG. 3(a), whereas being substantially fixed when the thickness hi is greater than or equal to 0.0178 m. The reason for this is that the influence of the strain induced primarily under the indenter increases as the thickness hi of the specimen decreases.

Figure 13:
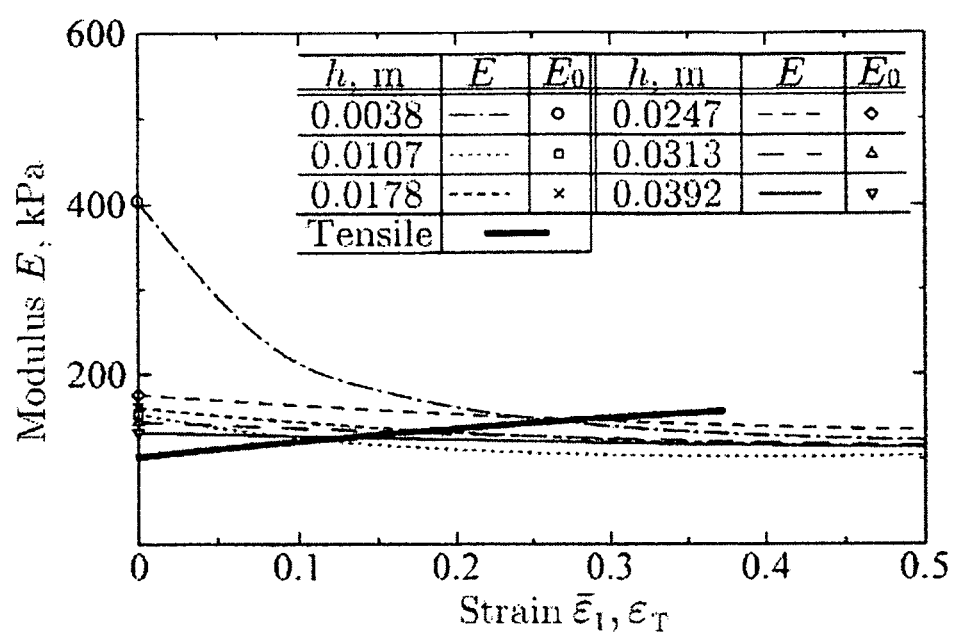
FIG. 13 shows the relationship between Young's modulus and equivalent indentation strain.

In comparison with the results shown in FIG. 12, FIG. 13 shows Young's modulus E determined by using the relationship between the equivalent indentation strain $\epsilon_I$ (overline)

expressed by Equation (19), which represents the influence of the strain induced primarily under the indenter, and Equation (23). The results shown in FIG. 13 are determined by first determining the equivalent indentation strain $\bar{\epsilon}_I$ from Equation (13), which is the sum of the Hertz strain $\bar{\epsilon}_H$ (overline), which is determined by substituting the indentation depth δ into Equation (5), and the rate of change $\bar{\epsilon}_V$ (overline) in the deformed region, and then substituting the equivalent indentation strain $\bar{\epsilon}_I$ and the measured force F into Equation (4).

As seen from the results shown in FIG. 13, the results for the thickness hi of the specimen greater than or equal to 0.0178 m do not greatly differ from the results shown in FIG. 12 based on the Hertzian elastic contact theory, whereas the results for the thickness hi smaller than or equal to 0.0107 m show that the Young's modulus E influenced by the thickness of the specimen and identified to be higher does not increase as the indentation proceeds but instead tends to decrease and converge to the values for specimens having large thicknesses. It is therefore believed that the equivalent indentation strain $\bar{\epsilon}_I$ (overline) well expresses the influence of the strain induced primarily under the indenter.

FIG. 13 also shows a thick solid line representing the Young's modulus E obtained in the tensile test described above, which differs from those in FIG. 13 described above due to the difference in testing method but is substantially the same level. Further, the same tendency is seen in FIG. 13, in which the Young's modulus E increases when a specimen is pulled, whereas decreasing when a specimen is compressed.

The experimental results described above indicate that in an indentation test in which a spherical indenter indents a soft material, adding the influence of the compression deformation that occurs in the specimen having a finite thickness primarily under the indenter to the contact deformation based on the Hertzian elastic contact theory allows the Young's modulus E to be identified irrespective of the thickness of the specimen.

A description will next be made of an indentation test method and an indentation test apparatus according to a second embodiment of the invention.

The indentation test method, which is a method for indenting a specimen with a spherical indenter, includes identifying the thickness of the specimen, calculating equivalent indentation strain of the specimen by using the thickness of the specimen, and calculating the Young's modulus of the specimen by using the equivalent indentation strain.

The indentation test apparatus, which is an apparatus for indenting a specimen with a spherical indenter, includes a specimen thickness identifier that identifies the thickness of a specimen, an equivalent indentation strain calculator that calculates equivalent indentation strain of the specimen by using the thickness of the specimen, and a Young's modulus calculator that calculates the Young's modulus of the specimen by using the equivalent indentation strain.

In the texts in the present specification, an alphabet with a hat character is described as "(alphabet) hat", an alphabet with an overline is described as "(alphabet) overline", and an alphabet with a second differential coefficient is described as "(alphabet) second differential coefficient".

A description will be made of a Young's modulus measuring method used in a spherical indentation test. A method based on the Hertzian elastic contact theory will first be described.

When a sufficiently hard spherical indenter intends a semi-infinite specimen, the relationship between the indentation force F and the indentation depth δ can be derived from the Hertzian elastic contact theory by using the diameter φ of the spherical indenter, the Young's modulus E of the specimen, and the Poisson ratio ν thereof as follows:

[Equation 27]

$$F = \frac{4}{3}\frac{E}{1-v^2}\left(\frac{\phi}{2}\right)^{\frac{1}{2}}\delta^{\frac{3}{2}} \qquad (27)$$

Figure 14:
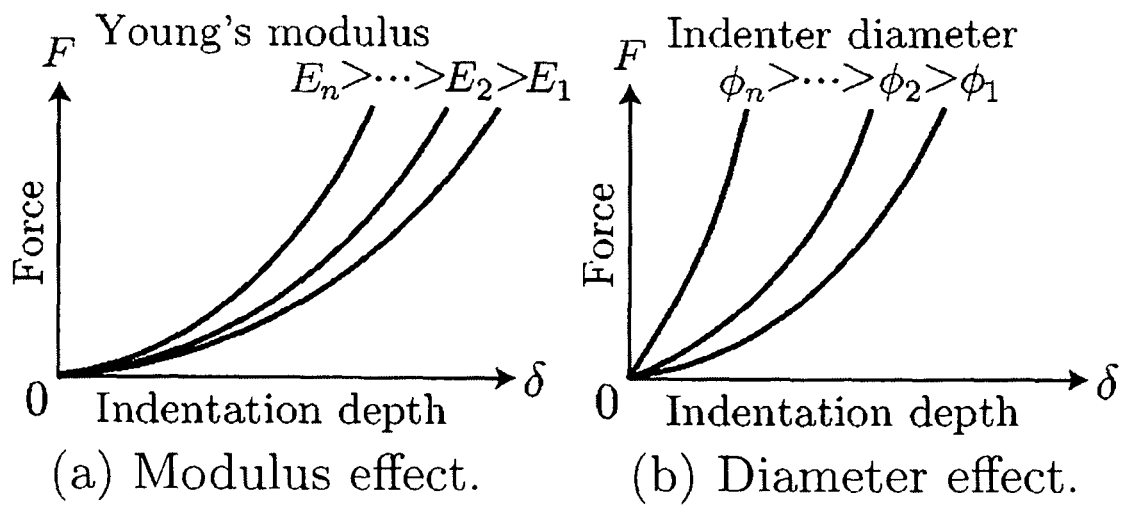
FIG. 14 shows influences of Young's modulus and the diameter of a spherical indenter on the relationship between the indentation force and the indentation depth.

Equation (27) represents the behavior of the indentation force F as shown in the diagrams of FIG. 14, in which the indentation force F decreases with the Young's modulus E of the specimen, whereas the indentation force F increases with the diameter φ of the spherical indenter. Examining the relationships between the force and the indentation depth allows Equation (27) to measure the Young's modulus E of the specimen.

A method based on the equivalent indentation strain will be described. The indentation force $\hat{F}$ (hat) acting on a finite specimen placed on a rigid body is greater than the indentation force F acting on a semi-finite specimen indicated by the solid line, and the influence of the rigid body appears in accordance with the thickness hi of the specimen (i=1, 2, . . . , ∞), as indicated by the broken lines in FIG. 15(a). To consider the influence of the thickness of the specimen, the deformation of a specimen in a spherical indentation test is assumed to be a superposition of contact deformation and compression deformation. In this process, equivalent indentation strain $\bar{\epsilon}_I$ (overline) representing equivalent uniaxial strain at the center of the contact area is defined by the following equation:

[Equation 28]

$$\bar{\epsilon}_I = \bar{\epsilon}_H + \bar{\epsilon}_V \qquad (28)$$

The first term, which represents the contact deformation caused by the spherical indenter, is derived from the Hertzian elastic contact theory and expressed by the following equation:

[Equation 29]

$$\bar{\epsilon}_H = -\frac{2}{\pi(1-v^2)}\left(\frac{2\delta}{\phi}\right)^{\frac{1}{2}} \qquad (29)$$

The second term, which represents the compression deformation that occurs between the spherical indenter and the rigid body, is expressed by the following equation:

[Equation 30]

$$\bar{\epsilon}_V = \frac{\delta}{h} - \frac{2}{3}\ln\left\{\frac{2h+3\left(\frac{\phi}{2}-\delta\right)}{2h+3\frac{\phi}{2}}\right\} \qquad (30)$$

Figure 15:
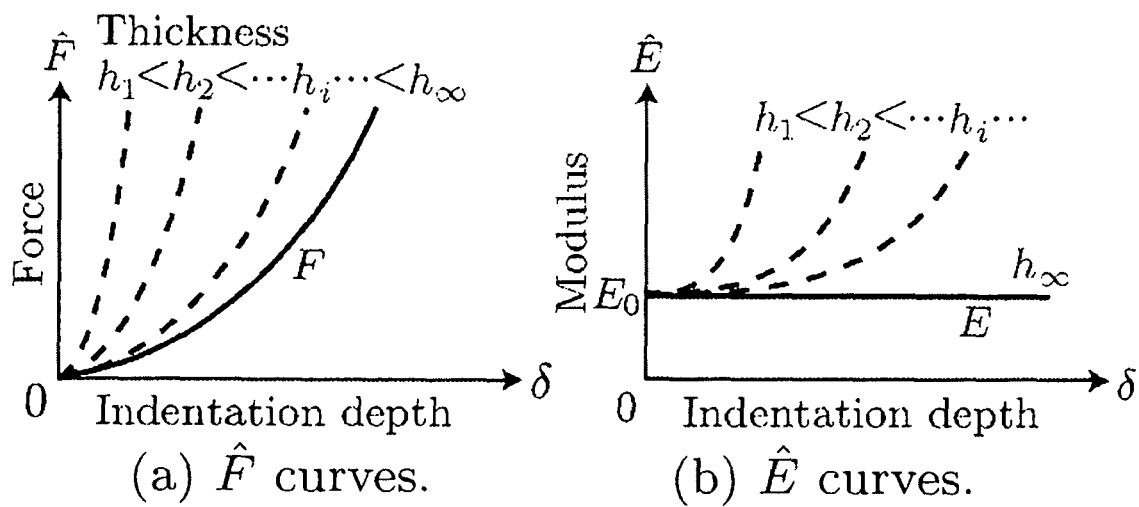
FIG. 15 shows an influence of the thickness of a specimen on the relationship between the indentation force and the indentation depth and between Young's modulus and the indentation depth.

Based on the phenomenon indicted by the broken lines shown in FIG. 15(a), in which the slope of the force curves increases as the thickness hi of the specimens decreases, consider the following equation, which is an extended Hertzian theoretical equation (27), by considering a function representing the indentation depth δ or apparent Young's modulus $\hat{E}$ (hat):

[Equation 31]

$$\hat{F} = \frac{4}{3}\frac{E}{1-v^2}\left(\frac{\phi}{2}\right)^{\frac{1}{2}}\{\delta(1+B\delta)\}^{\frac{3}{2}} \quad (31)$$
$$= \frac{4}{3}\frac{\hat{E}}{1-v^2}\left(\frac{\phi}{2}\right)^{\frac{1}{2}}\delta^{\frac{3}{2}}$$

The following relationship is satisfied between the intrinsic Young's modulus E and the apparent Young's modulus E (hat):

[Equation 32]

$$E(1+B\delta)^{3/2} = \hat{E} \quad (32)$$

Equation (32) represents a phenomenon in which the intrinsic Young's modulus E and the apparent Young's modulus E (hat) have the same value $E_0$ when the contact starts, whereas the apparent Young's modulus E (hat) is measured to be greater than the intrinsic Young's modulus E as the indentation proceeds, as shown in FIG. 15(b).

Figure 16:
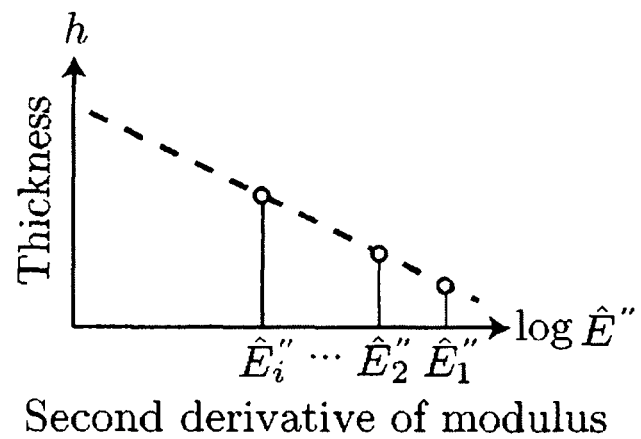
FIG. 16 shows the relationship between the thickness of a specimen and the second derivative of Young's modulus at the time of contact.

The relationship in the phenomenon between the thickness h of the specimen and the second derivative of Young's modulus E (hat) (second differential coefficient) at the time of contact has been found to be approximated by using an exponential relationship shown in FIG. 16. The exponential relationship is expressed as follows:

[Equation 33]

$$h(\hat{E}'') = H\ln\left(\frac{G}{\hat{E}''}\right) \quad (33)$$

In Equation (33), G represents a coefficient that normalizes the second derivative of Young's modulus, and H represents a coefficient for the thickness of the specimen.

The thickness h of the specimen is therefore determined by substituting the second derivative of Young's modulus E (hat) (second differential coefficient) at the time of contact into Equation (33), and the equivalent indentation strain $\epsilon_I$ (overline) expressed by Equation (28) is also determined from the thickness h of the specimen. Further, the equivalent indentation strain $\epsilon_I$ (overline) and the indentation force F (hat) can be used to determine Young's modulus E of the specimens having a variety of thicknesses by using the following equation:

[Equation 34]

$$E = -\frac{6}{\pi^3(1-v^2)^2}\left(\frac{2}{\phi}\right)^2\frac{\hat{F}}{\bar{\epsilon}_I^3} \quad (34)$$

It has been ascertained based on experimentally validated results obtained from specimens having a variety of thicknesses that the Young's modulus determined by using Equation (34) does not depend on thickness [1]. Further, if the measuring method can be used with a variety of hardness values and shapes, a specimen having a complicated deformation characteristic and shape, such as biological soft tissue, can be evaluated by the measuring method.

To study the hardness of a specimen and the diameter of the indenter that can be used with the measuring method, the influence of the Young's modulus E of a specimen and the diameter ϕ of a spherical indenter used in a test on the measuring method will next be experimentally evaluated. In particular, since the influence described above is found as a change in each force-indentation depth curve shown in FIG. 14, an influence of the change on Equation (33) representing the thickness of a specimen is evaluated and extended. Further, the validity of the extension is checked by comparing it with measurement results obtained in a tensile test.

Experimental evaluation of the applicability of the measuring method will be described. A spherical indentation test will first be described.

To check the applicability of the Young's modulus measuring method used in a spherical indentation test, experiments are conducted with the hardness of a specimen and the diameter of the indenter changed.

First, as for a specimen used in the evaluation, a commercially available silicone rubber (silicone rubber sheet manufactured by Kyowa Industries, Inc.) is used because it has stable physical properties, a wide variety of hardness values, and excellent moldability. Among the variety of sheets, three types of sheet having different hardness values shown in Table 5 are prepared, and a plurality of specimens having different thicknesses are prepared by bonding an arbitrary number of specimens having a square shape each side of which is 100 mm and a thickness of 1 mm and 5 mm with the aid of the viscosity of the specimens themselves. The specimens are then checked to have no discontinuity between the bonded surfaces due to separation or other causes during and after a test.

Figure 17:
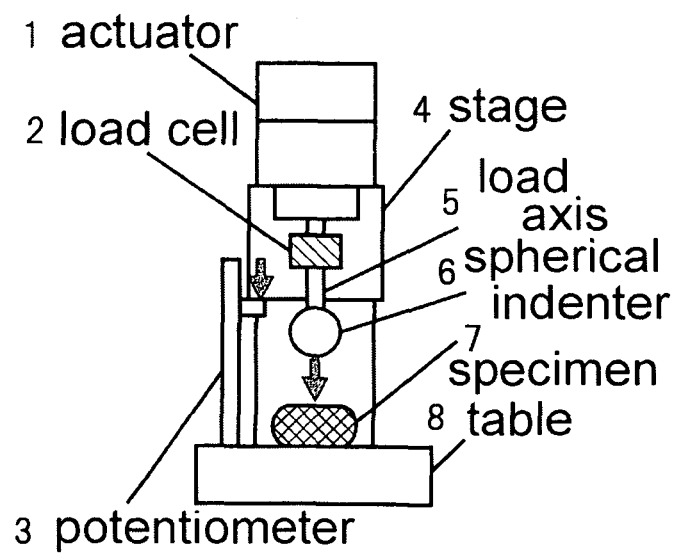
FIG. 17 schematically shows an indentation test apparatus.

FIG. 17 schematically shows an indentation test apparatus. The indentation test apparatus is so configured that a PC controls a load axis 5 attached to an actuator 1 (manufactured by NSK, Model: Mechatronics Actuator XY-HRS400-RH202) that operates at a rate of 1.2 m/s at maximum) and a spherical indenter attached to the load axis is intended into a specimen placed on a table made of a 2000-based aluminum, which can be considered as a rigid body. A load cell 2 (manufactured by Kyowa Electronic Instruments Co., Ltd., Model: LUR-A100NSA1) attached to the axis produces a load, and a potentiometer 3 (manufactured by Alps Electric Co., Ltd., Model: Slide Volume RSA0N11S9002) measures the indentation depth in the form of travel of a stage 4 of the actuator 1, to which the indenter is attached. The load resolution of the load cell 2 is $6.15 \times 10^{-3}$ N, and the displacement resolution of the potentiometer 3 is $1.53 \times 10^{-6}$ m.

Figure 18:
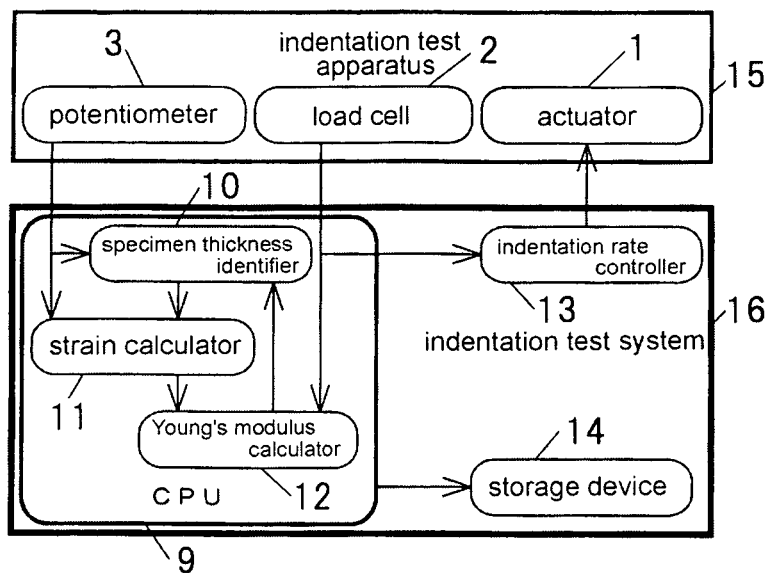
FIG. 18 shows the configuration of an indentation test system.

An indentation test system 16 calculates Young's modulus based on the magnitude of the force F sent from the load cell 2 and the indentation depth δ sent from the potentiometer 3 in the indentation test apparatus 15, as shown in FIG. 18. An indentation rate controller 13 in the indentation test system 16 controls the operation of the indentation test apparatus 15 at the same time. The thickness of the specimen is identified based on the thus sent indentation depth δ and calculated Young's modulus. Based on the identified and calculated thickness of the specimen, strain is calculated in consideration of the influence of the thickness of the specimen, and the Young's modulus is calculated in consideration of the influence of the thickness of the specimen. The data handled by a CPU 9 are all recorded in a storage device 14.

The experiments are conducted under the conditions that the diameter of the indenter has five different values shown in Table 6 and the friction between the specimen and the spherical indenter that come into contact with each other is reduced by applying talc powder onto the contact surface. The following two spherical indenters are used: an acrylic sphere made by the inventors and a ball knob made of a phenolic resin manufactured by Esco Co., Ltd. Further, the slowest indentation rate available in the apparatus specifications, $1.0 \times 10^{-4}$ m/s, is selected to reduce the influence of the viscosity of the specimen.

TABLE 5

Hardness and thickness of specimen

| Durometer hardness (Shore A hardness) | A20, A30, A50 |
|---|---|
| Thickness h, $10^{-3}$ m | 1, 2, 3, 4, 5, 6, 7, 8, 9, 10, 15, 20, 25, 30, 35, 40, 45 |

TABLE 6

Diameter and material of spherical indenter

| Diameter φ, $10^{-3}$ m | 20 | 25, 32, 38, 44 |
|---|---|---|
| Material | Acrylic resin | Phenolic resin |

Figure 19:
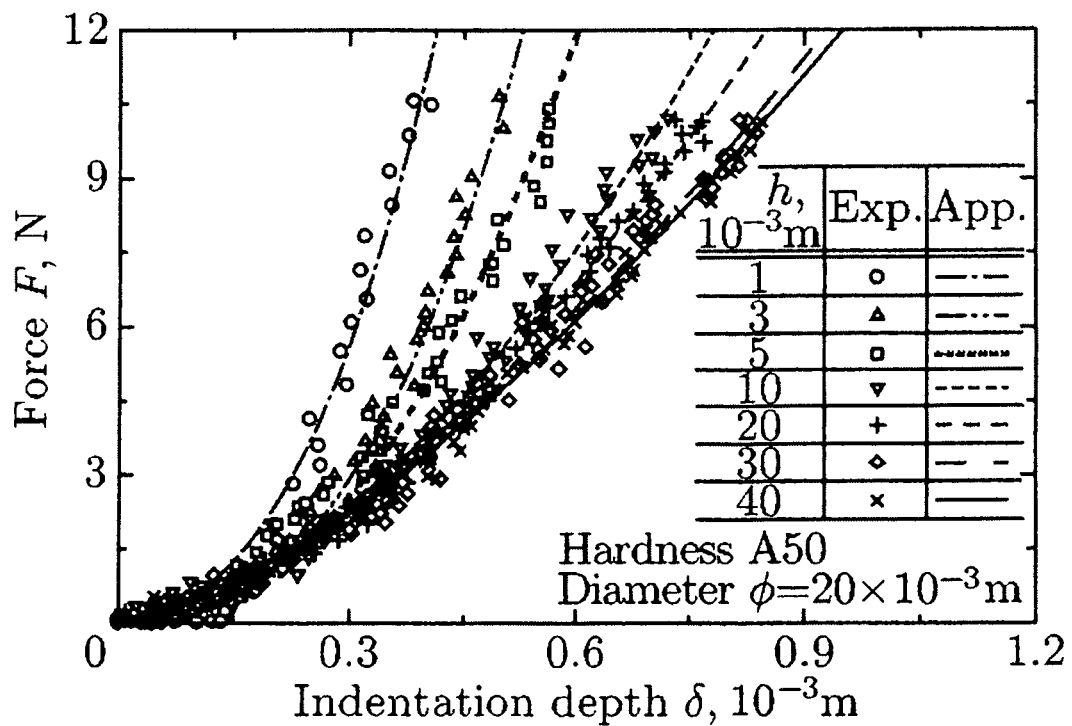
FIG. 19 shows the relationship between the indentation force and the indentation depth.

As an example of experimental results, FIG. 19 shows force-indentation depth curves for a hardness of A50 and a spherical indenter diameter φ of 20 mm. FIG. 19 also shows curves representing the experimental results having undergone least squares approximation based on Equation (31) on the assumption that the Poisson ratio is 0.4 for convenience. The force curves for specimens having a thickness h greater than or equal to 30 mm substantially agree with each other, but when the thickness h is smaller, the force more greatly increases as the indentation proceeds, as shown in FIG. 15(a).

To check how well the experimental results correlate with the approximated curves, correlation coefficients are calculated. A specimen having a large thickness shows a correlation coefficient greater than 0.98, whereas a specimen having a thickness of 1 mm shows about as low as 0.92. In view of the results described above, specimens having a correlation coefficient greater than 0.95 and a thickness greater than or equal to 4 mm are used to evaluate the applicability of the measuring method according to the invention by conducting experiments with the hardness of the specimens and the diameter of the spherical indenter changed.

Figure 20:
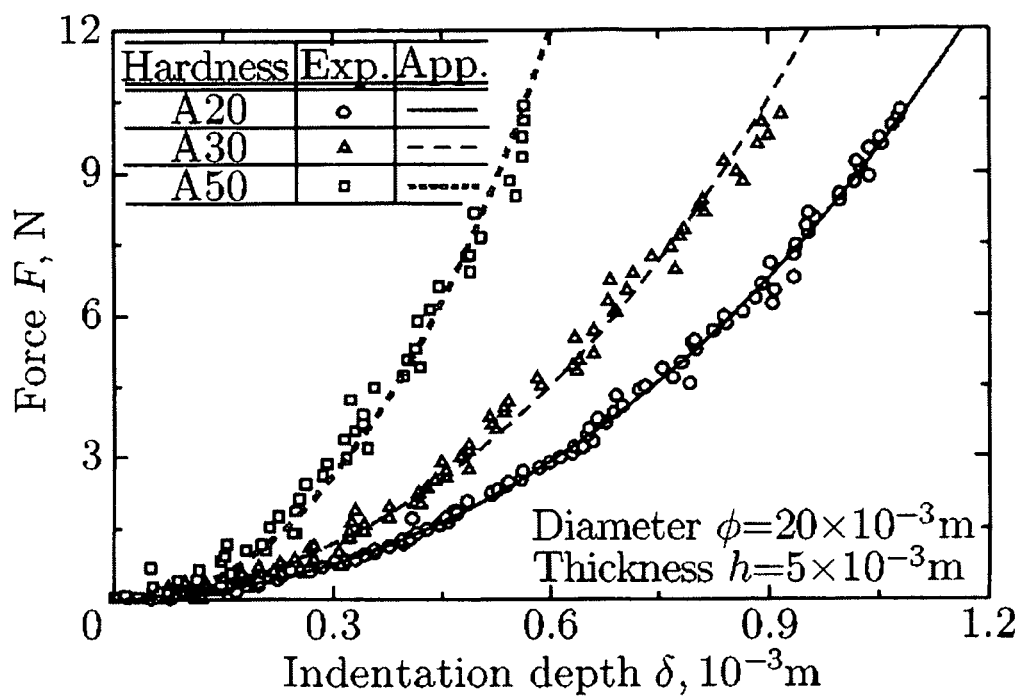
FIG. 20 shows an influence of the hardness of a specimen or the diameter of an indenter on the relationship between the indentation force and the indentation depth.
Figure 20:
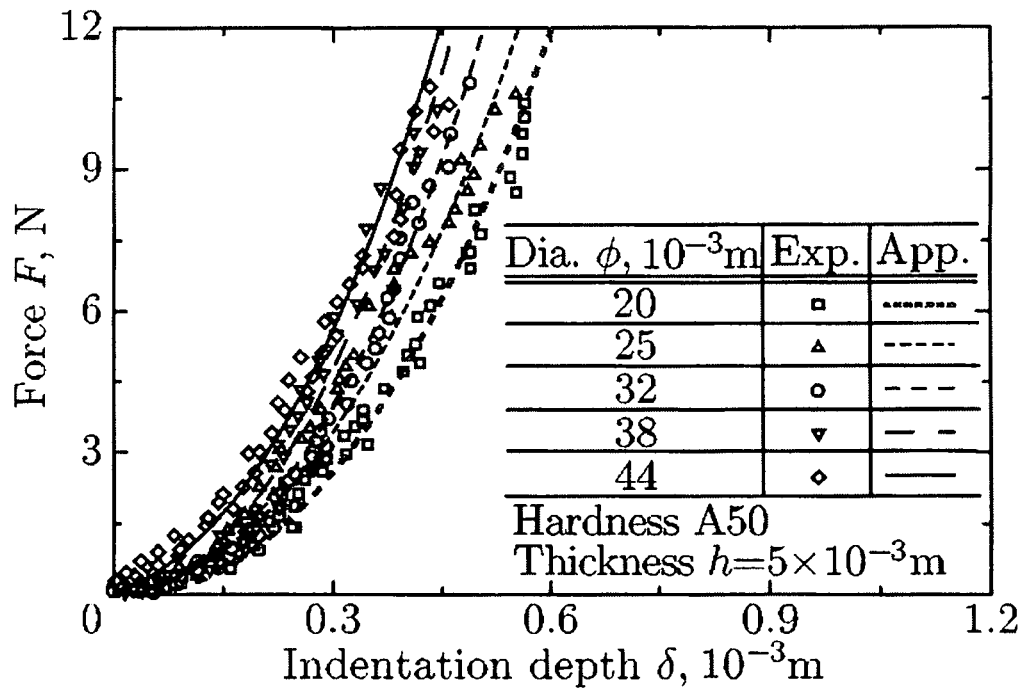

A method for evaluating the influence of the Young's modulus and the diameter of the indenter will be described. To observe the influence of the hardness of a specimen and the diameter of the indenter on a force curve, part of the change in the force obtained in an indentation test is shown in FIG. 20. FIG. 20(a) shows results under the conditions that the thickness of the specimen h is 5 mm and the diameter φ of the spherical indenter is 20 mm, and it is observed that when the hardness of the specimen is low, the indentation force becomes small. FIG. 20(b) shows results under the conditions that the thickness h of the specimen is 5 mm and the hardness of the specimen is A50, and the indentation force increase as the diameter φ of the spherical indenter. The results described above demonstrate that the hardness of the specimen and the diameter of the indenter influence the indentation force, as shown in the diagram of FIG. 14.

Consider next how the change in the force curve in FIG. 20 resulting from the difference in the hardness of the specimen and the diameter of the indenter influences the second derivative of Young's modulus E (hat) (second differential coefficient) at the time of contact and the thickness h of the specimen determined by Equation (33).

Figure 21:
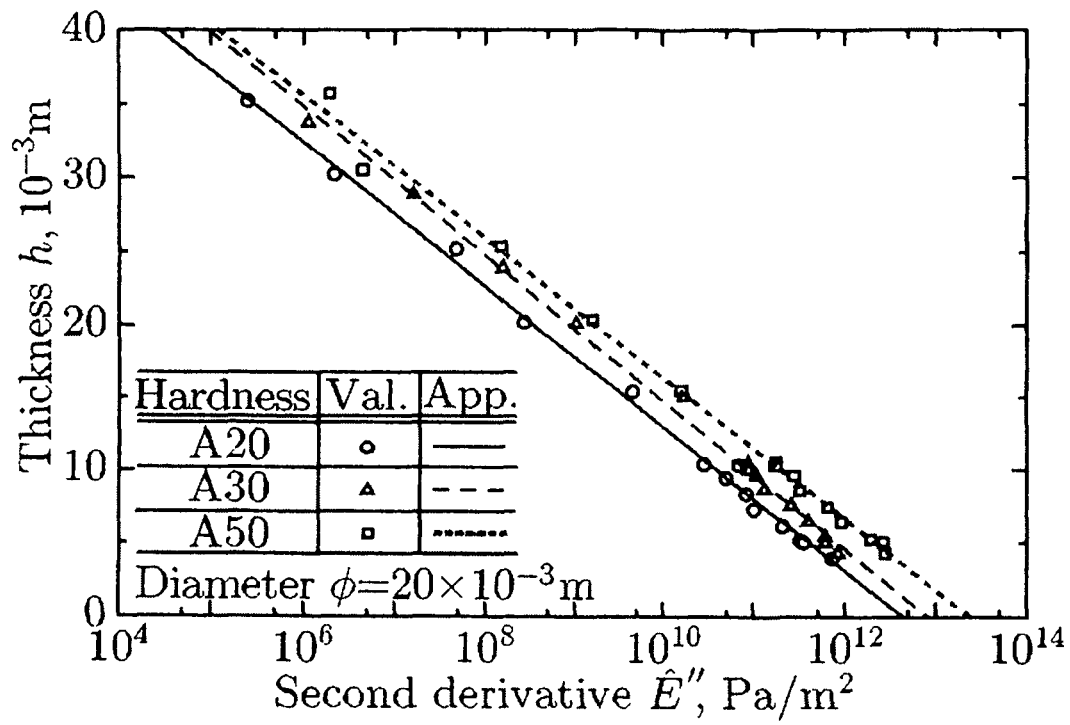
FIG. 21 shows the relationship between the thickness of a specimen and the second derivative of Young's modulus at the time of contact.
Figure 21:
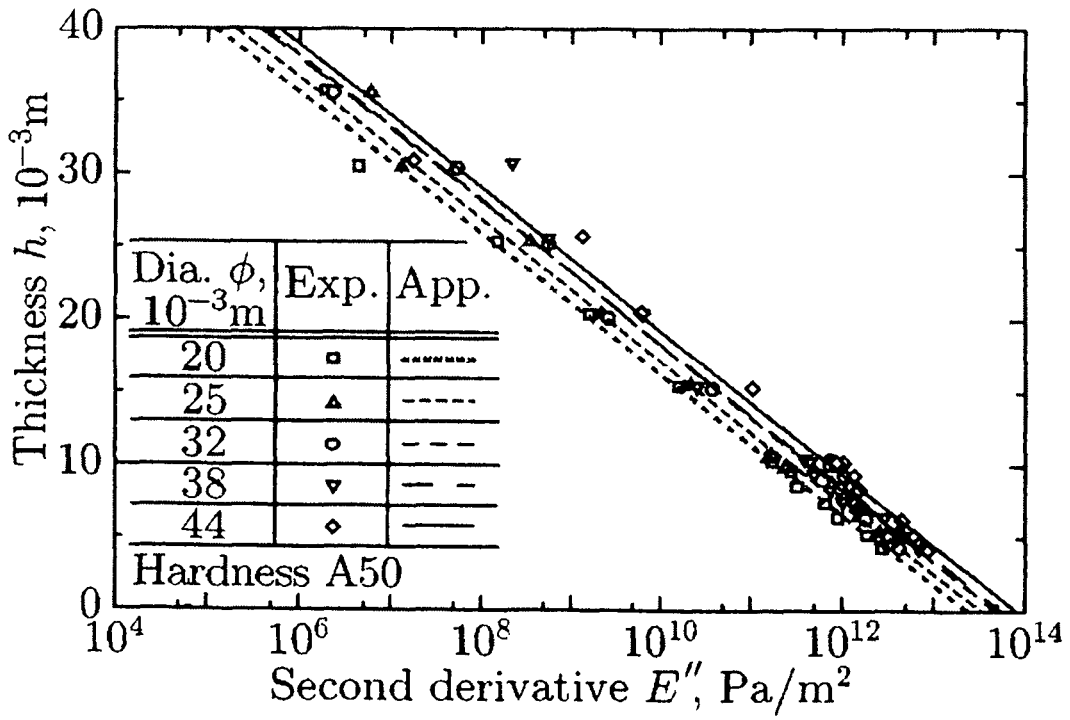

First, FIG. 21 shows the relationship between the actual thickness h of the specimen and the second derivative of Young's modulus E (hat) (second differential coefficient) at the time of contact obtained from the force curves shown in FIG. 20. Specifically, FIG. 20(a) shows results when the spherical indenter has a diameter φ of 20 mm, and FIG. 20(b) shows results obtained when the specimen has a hardness of A50. FIG. 21 also shows straight lines representing the experimental results having undergone least squares approximation based on Equation (33). The results indicate that the second derivative E (hat) (second differential coefficient) increases with the hardness of the specimen for the same diameter φ of the indenter, whereas the second derivative E (hat) (second differential coefficient) increases with the diameter φ of the spherical indenter for the same hardness of the specimen.

Figure 22:
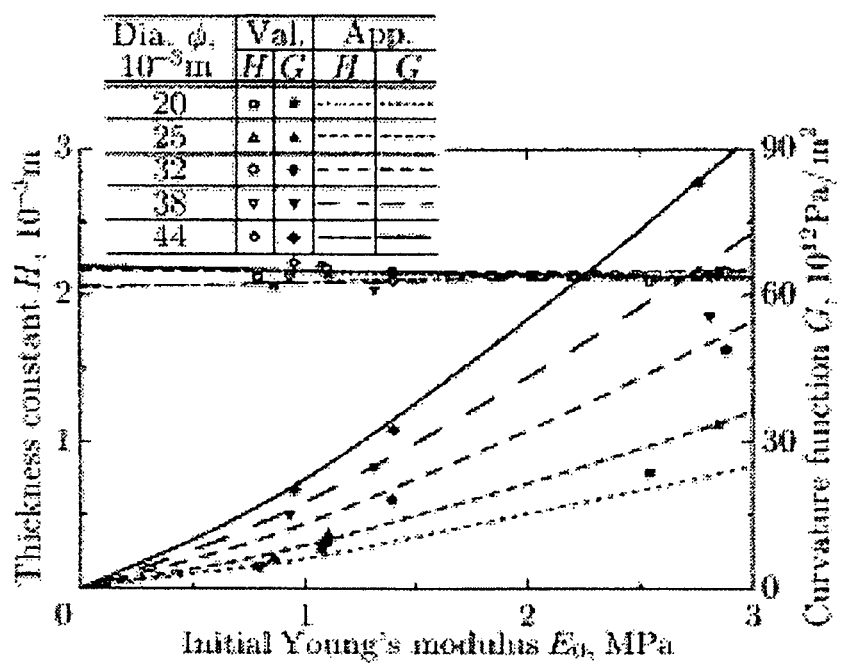
FIG. 22 shows how the hardness of a specimen or the diameter of an indenter influences variables H and G in an expression representing the relationship between the thickness of the specimen and the second derivative of Young's modulus at the time of contact.
Figure 22:
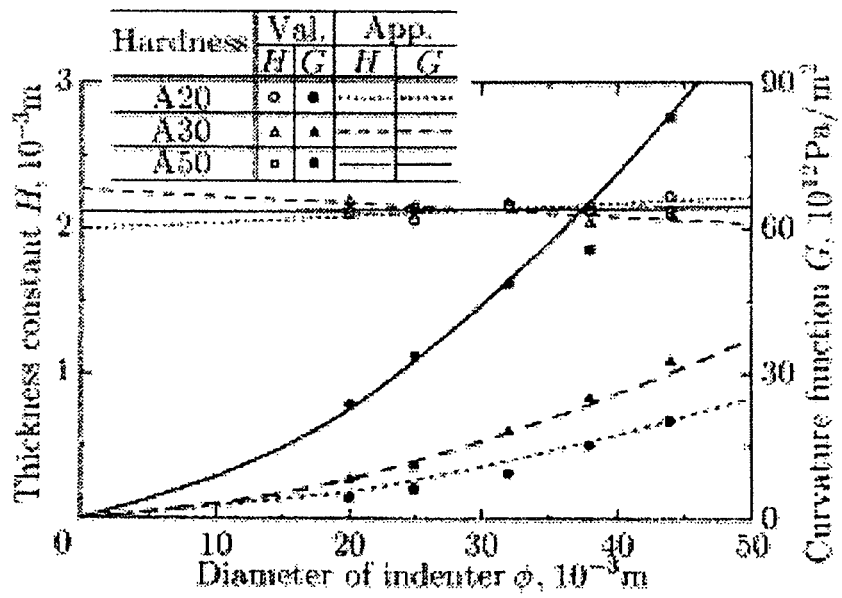

FIG. 22 shows how the variables H and G in Equation (33), which is used to provide the approximated straight lines shown in FIG. 21, are influenced. In FIG. 22(a), the horizontal axis represents the Young's modulus $E_0$ at the time of contact obtained from Equation (31). FIG. 22(a) shows that the variable H linearly changes with the diameter φ of the spherical indenter, and the variable G exponentially increases with the Young's modulus $E_0$. FIG. 22(b), in which differences in the variables H and G resulting from the change in the diameter φ of the spherical indenter are shown for each hardness value, shows that the variable H linearly changes with the hardness, and the variable G exponentially increases with the diameter φ of the spherical indenter. These results indicate that the variables H and G are both influenced by the Young's modulus $E_0$ at the time of contact and the diameter φ of the spherical indenter, but assume that the variable H, which is influenced relatively little, is a fixed coefficient, and that the variable G is defined by a function of the Young's modulus $E_0$ of a specimen at the time of contact and the diameter φ of the spherical indenter.

In the invention, the coefficient H is called a specimen thickness constant, and the function G is called a Young's modulus curvature function. The variables H and G are expressed by the following Equations (35) and (36):

[Equation 35]

$$H = 2.13 \times 10^{-3}, m \qquad (35)$$

$$G(E_0, \phi) = \overline{G} E_0^m, \phi^n, Pa/m^2 \qquad (36)$$

In Equations (35) and (36), G (overline)=$7.32 \times 10^7$, m=1.29, and n=1.66.

As a result, the Young's modulus measuring method using equivalent indentation strain used in a spherical indentation test can be extended to a method that takes into consideration of the influence of the Young's modulus $E_0$ of a specimen and the diameter φ of the spherical indenter by using Equation (36).

Measured Young's modulus will now be described. The validity of the evaluation method described above, in which the influence of the Young's modulus and the diameter of the indenter are considered, is examined by comparing obtained the Young's modulus with that obtained in a tensile test.

First, a system used in a tensile test conducted on a material to be evaluated is substantially the same as the indentation test apparatus shown in FIG. 17 but dedicated to a soft material, such as biological soft tissues [2]. In the system, a laser displacement gauge (manufactured by KEYENCE, Model: LB-62) measures an inter-chuck displacement used to calculate strain, and a load cell (manufactured by Kyowa Electronic Instruments Co., Ltd., Model: Microforce Load Cell LST-1KA) measures the force. The displacement resolution of the laser displacement gauge is $6.25 \times 10^{-6}$ m, and the load resolution of the load cell is $3.28 \times 10^{-3}$ N. Each specimen is cut into a 1-mm square strip, the inter-chuck distance is set at 20 mm, and the tensile rate is set at $1.0 \times 10^{-4}$ m/s.

Figure 23:
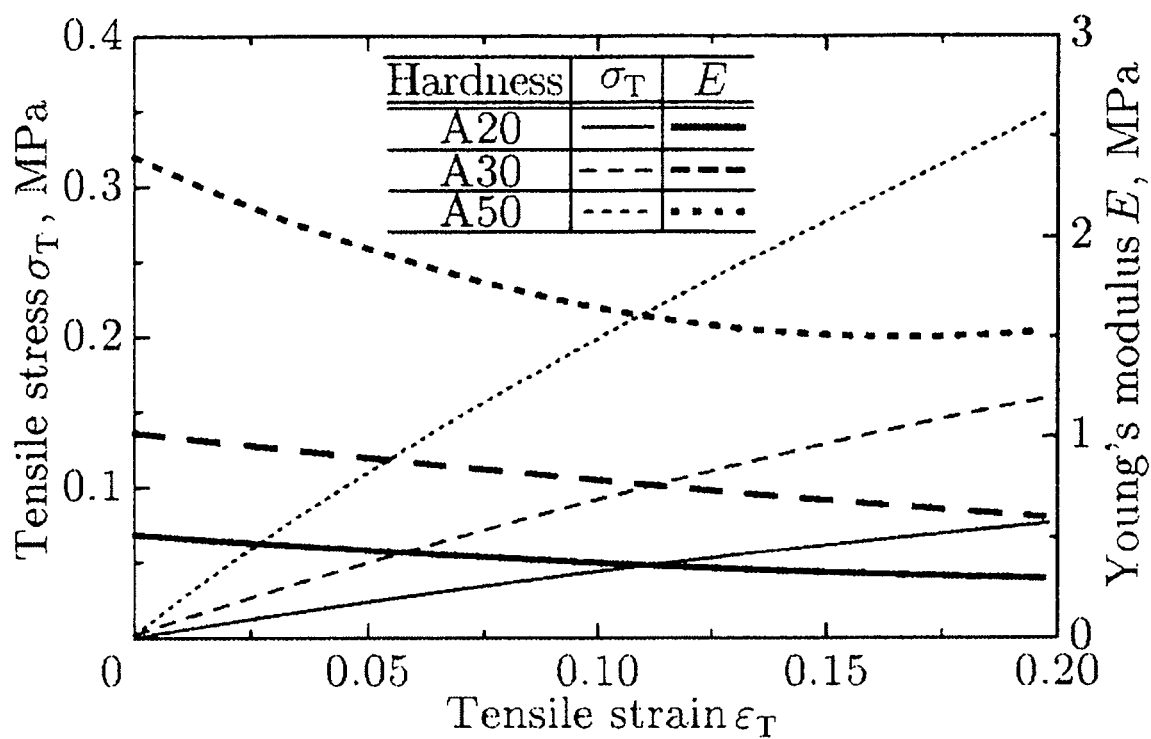
FIG. 23 shows results of a tensile test.

FIG. 23 shows nominal stress-nominal strain curves representing results of the tensile test conducted under the conditions described above. The resultant curves have slightly upward convex shapes, and the resultant Young's modulus E indicated by the thick lines tends to decrease as the strain ET increases.

Figure 24:
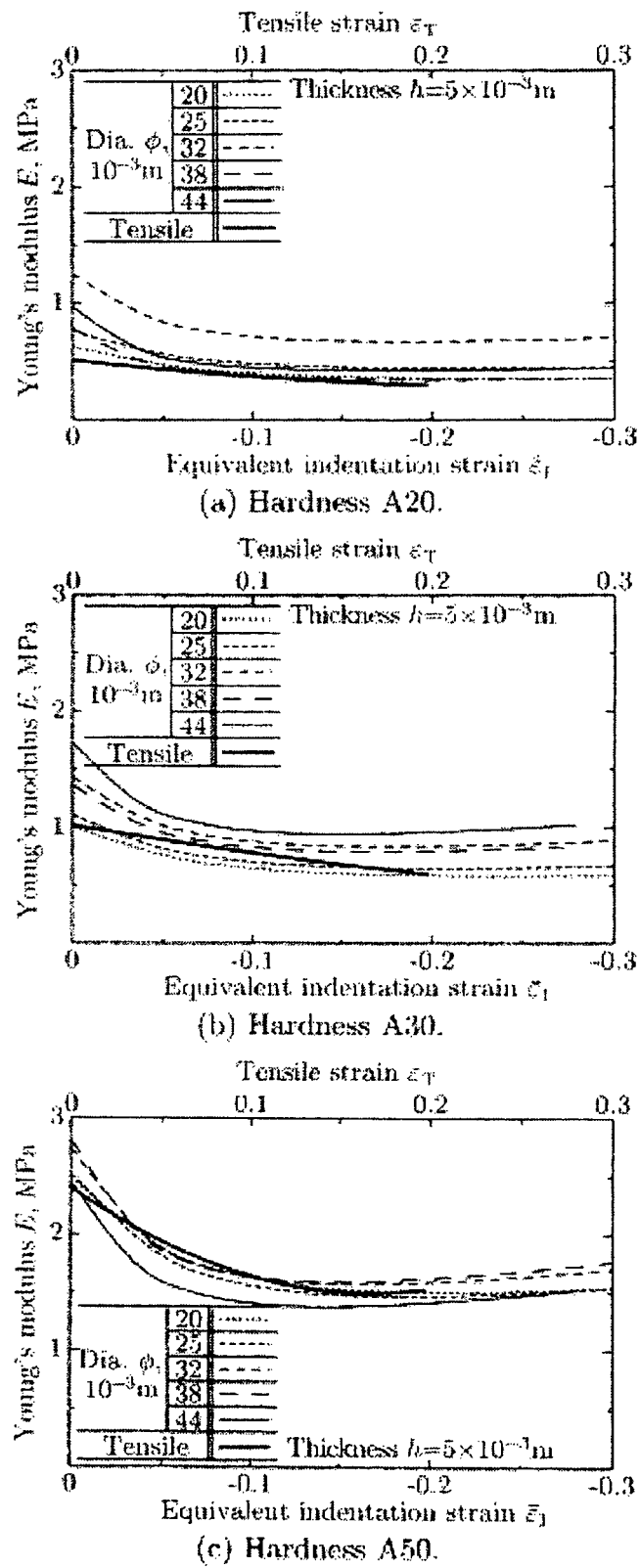
FIG. 24 shows the relationship between Young's modulus and an equivalent indentation strain.

FIG. 24 shows the Young's modulus calculated by using Equation (33) derived in consideration of the influence of the Young's modulus of a specimen and the diameter of the indenter. FIG. 23 also shows the Young's modulus measured in tensile tests.

FIGS. 24(a), 24(b), and 24(c) show measurement results for a specimen having a thickness h of 5 mm. The results shown in FIGS. 24(a), 24(b), and 24(c), which are drawn for different hardness values of specimens, show that the measurement results are substantially the same as those obtained in the tensile tests. Further, looking at an influence of the difference in the diameter φ of the spherical indenter, one can see that the measurement results obtained with the Young's modulus and the diameter of the indenter changed are close to the results obtained in the tensile tests although one sees that initial values vary in accordance with the precision at the time of contact, as in the previous report [1], whereby the validity of the extended Equation (36) can be checked.

Looking at the results shown in FIG. 24, one can see that the dependence of the Young's modulus obtained in the present measuring method on the strain agrees with that of the results obtained in the tensile tests, that is, the Young's modulus increases or decreases in the same manner, and can observe a softening phenomenon due to the strain. Further, in FIG. 24(c), in which the hardness is A50, a point of inflection where hardening starts is located in the vicinity of a strain of −0.15 in the tensile test, whereas the point of inflection can be similarly measured in the present measuring method although located in the vicinity of a strain of −0.11.

Examples of the specimen to be tested by using the indentation test method and the indentation test apparatus according to the invention may include polyurethane, silicone rubber, polyolefin rubber, natural rubber, soft vinyl, and other polymer materials; skin, muscle, and other biological tissues; and jelly, gelatin, and other food products.

The Young's modulus E of a specimen preferably ranges from 100 Pa to 100 MPa. An advantage from the Young's modulus of a specimen being greater than or equal to 100 Pa is that the specimen will not collapse or break as indentation proceeds. An advantage from the Young's modulus of a specimen being smaller than or equal to 100 MPa is that a soft indenter can also be used.

The spherical indenter can, for example, be made of a metallic material and/or a resin material.

The diameter of the spherical indenter preferably ranges from $1 \times 10^{-8}$ to 1 m. An advantage from the thickness of a specimen being greater than the diameter of the spherical indenter is that results are equivalent to those based on the Hertzian theoretical solution. An advantage from the thickness of a specimen being smaller than or equal to the diameter of the spherical indenter is that the Young's modulus that cannot be determined by using the Hertzian theory can identified.

The rate at which the spherical indenter is indented preferably ranges from 0.00001 to 10 m/s. An advantage from the rate at which the spherical indenter is indented being higher than or equal to 0.00001 m/s is that the measurement can be made in a short period. An advantage from the rate at which the spherical indenter is indented is lower than or equal to 10 m/s is that the apparatus can be operated in a safe manner.

The ratio of the indentation depth of the spherical indenter to the diameter of the spherical indenter is preferably smaller than or equal to one. An advantage from the ratio being smaller than or equal to one is that it is unnecessary to consider a case where the indenter is buried.

To reduce the adhesion between the spherical indenter and a specimen when they come into contact with each other, for example, talc powder or oil may be applied onto the surface of the specimen where it comes into contact with the indenter. When the adhesion between the spherical indenter and a specimen when they come into contact with each other is low, the process described above can be omitted.

The above description has been made with reference to the case where the indenter has a spherical shape, but the indenter is not limited to a spherical indenter. The shape of the indenter may alternatively be, for example, a solid cylinder, a hollow cylinder, or a cube.

In the indentation test method and the indentation test apparatus according to the invention, the thickness of a specimen is identified. Advantages from identifying the thickness of a specimen may, for example, be an ability to identify the Young's modulus, which is difficult to determine based on the Hertzian theory, and an ability to measure the state of skin or muscle in a noninvasive manner, which is required in human diagnosis.

The method for identifying the thickness of a specimen is not limited to that described above. Other methods for identifying the thickness of a specimen may include a method using an ultrasonic wave, X-rays, or MRI. Further, a method for optically measuring a cross section of a specimen and all other methods typically used to measure the thickness of a specimen can be used.

The mode for carrying out the invention described above can, of course, be replaced with a variety of other configurations without departing from the substance of the invention.

REFERENCE DOCUMENTS

[1] M. Tani and A. Sakuma, M. Shinomiya, Evaluation of Thickness and Young's Modulus of Soft Materials by using Spherical Indentation Testing, Transactions of the Japan Society of Mechanical Engineers, Series A, Vol. 75, No. 755, (2009), pp. 901-908. (in Japanese)

[2] M. Ogasawara, A. Sakuma, T. Tadomi, E. Yanagisawa and M. Tani, Valuation Technique of Nonlinear Parameters in Three-Element Solid Model and Its Application to Biological Soft Tissue, Transactions of the Japan Society of Mechanical Engineers, Series A, Vol. 75, No. 750, (2009), pp. 251-258. (in Japanese)

DESCRIPTION OF SYMBOLS

1: actuator
2: load cell
3: potentiometer
4: stage
5: load axis
6: spherical indenter
7: specimen
8: table
9: CPU
10: specimen thickness identifier
11: equivalent indentation strain calculator
12: Young's modulus calculator
13: indentation rate controller 14: storage device
15: indentation test apparatus
16: indentation test system

What is claimed is:

1. A method of calculating a Young's modulus of a material specimen that is a biological soft tissue, the method comprising:
   indenting the material specimen with an indenter attached to a load axis actuated by an actuator;
   obtaining an indentation force of the indenter using a load cell attached to the load axis;
   obtaining, using a potentiometer, an indentation depth of the indenter into the material specimen based on a travel of the indenter;
   obtaining, as a strain induced by compression deformation, a rate at which a compressed region in the material specimen changes, the compressed region being a region in the material specimen that is compressed and deformed by a load from the indenter;
   obtaining, as a strain induced by contact deformation, a strain induced when the indenter comes into contact with the material specimen;
   summing the strain induced by compression deformation and the strain induced by contact deformation to determine an equivalent indentation strain of the material specimen; and
   calculating, using a Young's modulus calculator, the Young's modulus of the material specimen using the equivalent indentation strain of the material specimen, wherein
   the strain induced by compression deformation is defined by $$\bar{\varepsilon}_V = \int_0^\delta d\varepsilon_V = \frac{\delta}{h} + \frac{2}{3}\ln\left\{\frac{2h+3\left(\frac{\phi}{2}-\delta\right)}{2h+3\frac{\phi}{2}}\right\}$$

where $\phi$ is a diameter of the indenter, h is a thickness of the material specimen, and $\delta$ is the indentation depth of the indenter into the material specimen,
   the strain induced by contact deformation is defined by $$\bar{\varepsilon}_H = \frac{2}{\pi(1-v^2)}\left(\frac{2\delta}{\phi}\right)^{\frac{1}{2}}$$

where $v$ is the Poisson ratio, and
   the Young's modulus is calculated by $$E = \frac{6}{\pi^3(1-v^2)^2}\left(\frac{2}{\phi}\right)^2\frac{\hat{F}}{\bar{\varepsilon}_I^3}$$

where $\epsilon_I$ is the equivalent indentation strain and F is the indentation force.

2. The indentation test method according to claim 1, further comprising identifying, using a specimen thickness identifier, the thickness of the specimen.

3. The indentation test method according to claim 1, wherein the indenter is a spherical indenter.

4. The indentation test method according to claim 3, wherein a diameter of the spherical indenter ranges from $1\times10^{-8}$ to 1 m.

5. The indentation test method according to claim 2, wherein the indenter is a spherical indenter, and the identification of the thickness of the specimen is performed by a calculation based on a diameter of the spherical indenter, a Young's modulus at the time of contact, and a second derivative of the Young's modulus.

6. The indentation test method according to claim 1,
   wherein the contact deformation is calculated based on a Hertz elastic contact theory, and
   wherein the compression deformation is the rate in the compressed region when the specimen is compressed, the rate being approximated by an indentation depth of the compressed region of the specimen.

7. The indentation test method according to claim 1, wherein the indenter is assumed to be rigid when calculating the equivalent indentation strain.

8. An indentation test apparatus for calculating a Young's modulus of a material specimen that is a biological soft tissue, the apparatus comprising:
   an actuator that actuates a load axis attached to an indenter to indent the material specimen with the indenter;
   a load cell that is attached to the load axis and obtains an indentation force of the indenter;
   a potentiometer that obtains an indentation depth of the indenter into the material specimen based on a travel of the indenter;
   an equivalent indentation strain calculator that i) obtains, as a strain induced by compression deformation, a rate at which a compressed region in the material specimen changes, the compressed region being a region in the material specimen that is compressed and deformed by a load from the indenter, ii) obtains, as a strain induced by contact deformation, a strain induced when the indenter comes into contact with the material specimen, and iii) sums the strain induced by compression deformation and the strain induced by contact deformation to determine an equivalent indentation strain of the material specimen; and
   a Young's modulus calculator that calculates the Young's modulus of the material specimen using the equivalent indentation strain of the material specimen, wherein
   where the equivalent indentation strain is a sum of strain induced by a compression deformation and a strain induced by a contact deformation,
   the strain induced by compression deformation is defined by $$\bar{\varepsilon}_V = \int_0^\delta d\varepsilon_V = \frac{\delta}{h} + \frac{2}{3}\ln\left\{\frac{2h+3\left(\frac{\phi}{2}-\delta\right)}{2h+3\frac{\phi}{2}}\right\}$$

where $\phi$ is a diameter of the indenter, h is a thickness of the material specimen, and $\delta$ is the indentation depth of the indenter into the material specimen,
   the strain induced by contact deformation is defined by $$\bar{\varepsilon}_H = \frac{2}{\pi(1-v^2)}\left(\frac{2\delta}{\phi}\right)^{\frac{1}{2}}$$

where $v$ is the Poisson ratio, and
   the Young's modulus is calculated by $$E = \frac{6}{\pi^3(1-v^2)^2}\left(\frac{2}{\phi}\right)^2\frac{\hat{F}}{\bar{\varepsilon}_I^3}$$

where $\epsilon_I$ is the equivalent indentation strain and F is the indentation force.

9. The indentation test apparatus according to claim 8, further comprising a specimen thickness identifier that identifies a thickness of the specimen.

10. The indentation test apparatus according to claim 8, where the indenter is a spherical indenter.

11. The indentation test apparatus according to claim 10, where the diameter of the spherical indenter ranges from $1\times10^{-8}$ to 1 m.

12. The indentation test apparatus according to claim 9, where the indenter is a spherical indenter, and the identification of the thickness of the specimen is performed by a calculation based on a diameter of the spherical indenter, Young's modulus at a time of contact, and a second derivative of Young's modulus at the time of contact.

13. The indentation test apparatus according to claim 8,
wherein the contact deformation is calculated based on a Hertz elastic contact theory, and
wherein the compression deformation is the rate in the compressed region when the specimen is compressed, the rate being approximated by an indentation depth of the compressed region of the specimen.

14. The indentation test apparatus according to claim 8, wherein the equivalent indentation strain calculator assumes that the indenter is rigid.

\* \* \* \* \*